United States Patent
Papp

(10) Patent No.: US 11,396,299 B2
(45) Date of Patent: Jul. 26, 2022

(54) VIDEO PROCESSING FOR VEHICLE RIDE INCORPORATING BIOMETRIC DATA

(71) Applicant: Dr. Ing. h.c. F. Porsche Aktiengesellschaft, Stuttgart (DE)

(72) Inventor: Ethan Papp, Fremont, CA (US)

(73) Assignee: Dr. Ing. h.c. F. Porsche Aktiengesellschaft

(*) Notice: Subject to any disclaimer, the term of this patent is extended or adjusted under 35 U.S.C. 154(b) by 84 days.

(21) Appl. No.: 17/065,622

(22) Filed: Oct. 8, 2020

(65) Prior Publication Data

US 2021/0331684 A1 Oct. 28, 2021

Related U.S. Application Data

(63) Continuation-in-part of application No. 16/857,250, filed on Apr. 24, 2020.

(51) Int. Cl.
| | |
|---|---|
| *B60W 40/08* | (2012.01) |
| *B60W 50/14* | (2020.01) |
| *A61B 5/11* | (2006.01) |
| *G08B 21/02* | (2006.01) |
| *A61B 5/18* | (2006.01) |

(52) U.S. Cl.
CPC .......... *B60W 40/08* (2013.01); *A61B 5/1118* (2013.01); *A61B 5/18* (2013.01); *B60W 50/14* (2013.01); *G08B 21/0211* (2013.01); *B60W 2040/0872* (2013.01)

(58) Field of Classification Search
CPC ........ H04N 7/188; G06V 20/49; G06V 20/56; G06F 16/7867; G06F 16/739; B60R 2300/302; B60R 2300/00; B60R 2300/304; B60R 2300/70
See application file for complete search history.

(56) References Cited

U.S. PATENT DOCUMENTS

| | | | | |
|---|---|---|---|---|
| 9,792,502 | B2* | 10/2017 | Newman | H04N 13/178 |
| 9,807,291 | B1* | 10/2017 | Tome | H04N 1/00204 |
| 9,996,750 | B2* | 6/2018 | Campbell | G06V 20/49 |
| 10,643,665 | B2* | 5/2020 | de Jong | G11B 27/28 |
| 10,645,468 | B1* | 5/2020 | Kislevitz | G11B 27/34 |
| 10,719,722 | B2* | 7/2020 | Molin | H04N 21/41422 |
| 10,755,121 | B2* | 8/2020 | Molin | H04N 21/4334 |
| 2003/0154009 | A1 | 8/2003 | Basir et al. | |

(Continued)

FOREIGN PATENT DOCUMENTS

| | | | | |
|---|---|---|---|---|
| CA | 3006652 | A1 * | 11/2018 | G01C 21/165 |
| GB | 2539646 | | 12/2016 | |

(Continued)

OTHER PUBLICATIONS

Non Final Office Action for U.S. Appl. No. 16/857,250, dated Feb. 24, 2022, 19 pages.

*Primary Examiner* — John Villecco
(74) *Attorney, Agent, or Firm* — RatnerPrestia

(57) ABSTRACT

A method includes capturing video data from a camera over a period of time while capturing motion data from a detector and biometric data from another detector over that same period of time. Then, the method additionally includes selecting a subset of the video data captured during the period of time, based on a corresponding subset of the motion data and/or biometric data. The method then proscribes storing this selected subset of video data in memory.

15 Claims, 14 Drawing Sheets

(56) References Cited

U.S. PATENT DOCUMENTS

| | | | |
|---|---|---|---|
| 2004/0015289 A1 | 1/2004 | Poland et al. | |
| 2005/0088291 A1 | 4/2005 | Blanco et al. | |
| 2008/0186382 A1 | 8/2008 | Tauchi et al. | |
| 2008/0231703 A1 | 9/2008 | Nagata et al. | |
| 2010/0060734 A1 | 3/2010 | Chou | |
| 2012/0154591 A1 | 6/2012 | Baur et al. | |
| 2012/0308209 A1* | 12/2012 | Zaletel | G11B 27/34 386/E5.028 |
| 2014/0028848 A1* | 1/2014 | Takenaka | G07C 5/0866 348/148 |
| 2014/0071279 A1 | 3/2014 | Mokashi et al. | |
| 2014/0072278 A1* | 3/2014 | Kramer | H04N 21/6125 386/240 |
| 2015/0035665 A1* | 2/2015 | Plante | G07C 5/008 340/438 |
| 2015/0105934 A1* | 4/2015 | Palmer | H04N 5/935 701/1 |
| 2016/0144788 A1 | 5/2016 | Perrin, III et al. | |
| 2016/0189752 A1* | 6/2016 | Galant | H04N 5/772 386/224 |
| 2016/0224834 A1* | 8/2016 | Adsumilli | G11B 27/031 |
| 2016/0225410 A1* | 8/2016 | Lee | H04N 21/21805 |
| 2017/0069147 A1* | 3/2017 | Palmer | B60R 1/00 |
| 2017/0109585 A1* | 4/2017 | Matias | G06V 20/47 |
| 2017/0229149 A1* | 8/2017 | Rothschild | G16H 40/63 |
| 2017/0340209 A1 | 11/2017 | Klassen et al. | |
| 2017/0351922 A1* | 12/2017 | Campbell | H04N 19/179 |
| 2017/0361709 A1* | 12/2017 | Plante | B60K 35/00 |
| 2018/0190323 A1* | 7/2018 | de Jong | G11B 19/20 |
| 2018/0213288 A1* | 7/2018 | Patry | H04N 1/00167 |
| 2018/0247471 A1* | 8/2018 | Palmer | H04N 5/935 |
| 2019/0147259 A1* | 5/2019 | Molin | G06F 16/7844 382/104 |
| 2019/0389307 A1* | 12/2019 | Plante | B60K 35/00 |
| 2020/0066305 A1* | 2/2020 | Spence | G11B 27/036 |
| 2021/0337114 A1* | 10/2021 | Papp | G06F 16/739 |
| 2022/0138474 A1* | 5/2022 | Verma | G11B 27/034 386/241 |

FOREIGN PATENT DOCUMENTS

| | | | | |
|---|---|---|---|---|
| JP | 2004191194 A | * | 7/2004 | |
| JP | 2009246503 A | * | 10/2009 | |
| JP | 2011146860 A | * | 7/2011 | |
| JP | 2016167771 A | * | 9/2016 | |
| JP | 6376005 B2 | | 8/2018 | |
| WO | WO-2012146273 A1 | * | 11/2012 | ......... H04N 1/00323 |
| WO | 19041155 | | 3/2019 | |
| WO | 2020033612 A1 | | 2/2020 | |

\* cited by examiner

VIDEO PROCESSING FOR VEHICLE RIDE INCORPORATING BIOMETRIC DATA

CROSS-REFERENCE TO RELATED APPLICATION

This application is a U.S. continuation-in-part application of U.S. patent application Ser. No. 16/857,250, filed Apr. 24, 2020, the contents of such application being incorporated by reference herein in their entirety.

TECHNICAL FIELD

The present subject matter relates to techniques and equipment to utilize a vehicle and resulting drive metadata from the vehicle and driver in order to curate a video.

BACKGROUND

The modern automobile in recent years has seen a massive expansion in the number of internal electronic systems. Expanding far beyond the emissions and diagnostic systems tracked by the on-board diagnostics (OBD) systems standardized in the OBD-II interface, these cutting-edge vehicles are filled with electronic control units (ECUs) that monitor and track nearly every movement or action within the vehicle. Angle of the steering wheel, accelerator and brake pedal depression, current engine horsepower, and multidimensional gravity force equivalents (g-forces) are all recorded. Some automobiles have even added additional sensors in order to provide performance improvement features such as active suspension, which previews the road and adjusts suspension for each wheel individually, all within milliseconds.

These automobile systems are now at least in-part electrical. In order for all of these systems to work in tandem to provide optimal performance, the ECUs that manage the systems communicate over a software bus. A software bus could be for example a Controller Area Network (CAN) bus. Computer busses in general operate by allowing systems connected to the bus, such as the ECUs, to send messages through the bus to other ECUs. Alternatively, an ECU can broadcast data over the bus.

This presents an interesting opportunity: a vast quantity of an automobile's operational data can be gathered by a single component, synthesized, and then utilized. The application of this data has generally been limited to improving operation of the automobile, but there is potential to use this data for non-performance purposes.

Coupled with the vast quantity of the automobile's operational data being utilized, the biometric data of the driver of the automobile can also be utilized. More particularly, some automobiles either are or will soon be capable of communicating with a smartwatch worm by a driver or passenger in the vehicle. For example, an Apple Watch can (or soon will) be configured to communicate with an Apple CarPlay software system within a vehicle. The Apple Watch is configured to monitor the wearer's heart rate and other biometric features, and, in view of the invention described herein, it would be desirable to transmit that biometric information to the Apple CarPlay software system within the vehicle. When the driver's heart rate increases by more than a pre-determined value, for example, it can be assumed that the driver is experiencing an exciting drive.

Changing focus, data collection in the modern age has skyrocketed, and in particular the collection of video data has expanded immensely. Hundreds if not thousands of hours of video are uploaded to major video-sharing platforms every minute—far more than any person, or any determined group of people, could ever hope to watch. Additionally, the space requirements for storing all of these video files are significant. Video storage platforms are pushing to improve video curation, in order to cut down on their digital storage needs. Consumers and creators of videos are also looking for curation improvements. People need to store videos, and additionally they need video files that are actually desirable to watch. Long tedious videos punctuated by moments of excitement are not likely to retain a consumer's interest.

Automated digital file curation has been seen as a way out of this data overload problem. Software to determine if a video, or part of a video, is entertaining or even worth watching based on real-world metadata, is virtually nonexistent. The real-world metadata can include the automobile's operational data as well as the biometric data of the driver of the automobile.

SUMMARY OF INVENTION

Hence, there is still a need for further improvement in technologies for video curation. Particularly, people who make videos of driving their vehicle tend to produce long videos, punctuated by moments of excitement. These exciting moments interestingly enough tend to correlate with something the vehicle itself is doing. An exciting pass can be linked to quick acceleration, a near-miss collision could associate with quick deceleration, and a well-cornered turn could be associated with both. Therefore, a system that utilizes the acceleration data of an automobile and/or heart rate (or other biometric data) of the driver of that automobile, collected simultaneously with a video of that automobile driving, could pick out exciting individual moments or scenes from within a longer video, based solely on that metadata. The system could then combine these smaller clips into a curated video, one that saves space, saves time, and improves on a viewer's enjoyment as compared to the uncurated video.

As a first example, a method for curating a video of a vehicle drive is provided. The method comprises capturing video data of the vehicle drive over a first period of time; capturing biometric data associated with a driver or passenger of the vehicle over the first period of time; selecting a first subset of the video data captured during the first period of time, based on a corresponding first subset of the biometric data captured during the first period of time, the first subsets each spanning a second period of time that is less than the first period of time; and storing the first subset of the video data.

As a second example, a video curation system for a vehicle is provided. The video curation system comprises an input device configured to receive motion data of the vehicle during a vehicle drive, and video data relating to the vehicle drive; a memory coupled to the processor; a display coupled to the processor; a user interface coupled to the processor; and programming in the memory. Execution of the programming by the processor configures the video curation system to implement functions, including functions to: capture video data over a first period of time; capture motion data over the first period of time; select a first subset of the video data captured during the first period of time based on a corresponding first subset of the motion data captured during the first period of time, the first subset of the video spanning a second period of time; store the first subset of the video data in the memory; present the first subset composition to a user via the display; and permit the user to adjust a start time and/or an end time of the first subset using the user interface.

Additional advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations, by way of example only, not by way of limitations. In the figures, like reference numerals refer to the same or similar elements.

FIG. 4A focuses on tagging based on vehicle acceleration, FIG. 4B focuses on determining and counting hard turns, FIG. 4C focuses on tagging based on biometric data, and FIG. 4D focuses on ancillary information uploaded from the vehicle and smartwatch.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The term "coupled" as used herein refers to any logical, optical, physical or electrical connection, link or the like by which signals or light produced or supplied by one system element are imparted to another coupled element. Unless described otherwise, coupled elements or devices are not necessarily directly connected to one another and may be separated by intermediate components, elements or communication media that may modify, manipulate or carry signals.

Reference now is made in detail to the examples illustrated in the accompanying drawings and discussed below.

Figure 1B:
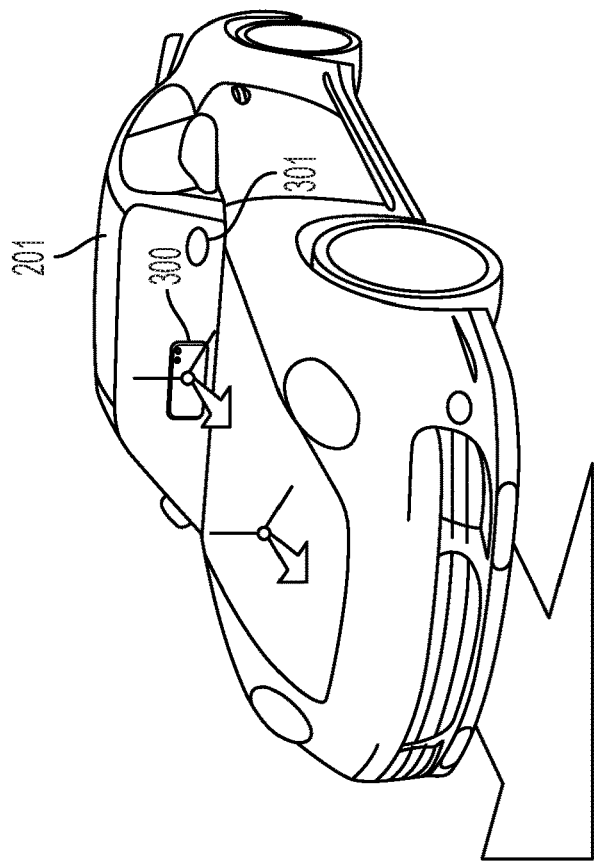
FIGS. 1A and 1B depict a vehicle with an embedded accelerometer, a mobile device above the vehicle's dashboard with an additional embedded accelerometer, and a smartwatch worn by a driver of the vehicle.
Figure 1A:
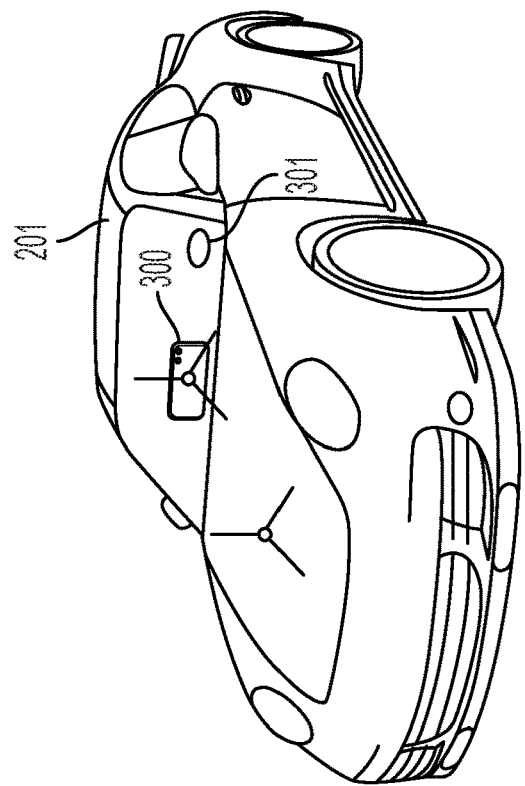

FIGS. 1A and 1B depict an electronic mobile device 300 (otherwise referred to herein as a smartphone) mounted to the windshield or dash board of a vehicle 201, and a smartwatch 301 that is worn by a driver of the vehicle 301. Data from the mobile device 300, smartwatch 301 and the vehicle 201 is used to create (i.e., curate) a video comprising video data (e.g., the road and surroundings either before, behind or beside the vehicle 201), motion data (e.g., speed, acceleration), biometric data (e.g., heart rate) and/or ancillary data (e.g., vehicle torque, vehicle power, drive gear selection, songs playing on vehicle radio). The video data, biometric data, motion data and ancillary data may be generated from the mobile device 300, the smartwatch 301 and/or the vehicle 201. With regard to the motion data, for example, both the mobile device 300 or the vehicle 201 include motion detectors or sensors (e.g., accelerometer and GPS chip) that can determine the location, speed and/or acceleration of the vehicle 201 as will be explained hereinafter.

There are at least three different ways to curate a video using the video data, biometric data and motion data. In a first example, video information produced by camera in the mobile device 300 is used in concert with motion information from sensors in the vehicle 201 and the biometric data from the smartwatch 301 to curate a video. The flowcharts of FIGS. 4A, 4B, 4D, and 5 relate to the first example. In a second example, video and motion information produced by the mobile device 300 and the biometric data from the smartwatch 301 are used to curate a video. The flowcharts of FIGS. 4C, 6 and 7 relate to the second example. In a third example, where a vehicle has a camera, video and motion information produced by the vehicle 201 (only) are used along with the biometric data from the smartwatch 301 to curate a video.

In the first example, communications between the mobile device 300, smartwatch 301 and vehicle 201 can be achieved by connecting the vehicle's Controller Area Network (CAN) bus to a wireless radio, such as a Wi-Fi radio, or a Bluetooth radio. The vehicle's wireless radio would then connect to the mobile device's radio, and send accelerometer data, either in bulk or in portions, to the mobile device 300 to aid in video curation. Also, the smartwatch 301 would connect to the mobile device's radio, and send biometric data, either in bulk or in portions, to the mobile device 300 to aid in video curation. Therefore, the vehicle 201 only need a means to transfer data from itself to mobile device 300 in order to use the mobile device 300 to aid in curation of the video. Mobile device 300 could perform the video curation. Alternatively, the vehicle's processors could perform the video curation, having received the uncurated raw video data from the mobile device 300 and biometric data from the smartwatch 301. This may improve processing, or reduce ease of unauthorized copying of the curation software. The curated video could then be sent back to the mobile device 300, or it could be sent directly to another server via Wi-Fi or 4G/LTE radios built into the vehicle 201.

In the second example, where the accelerometer or other sensors of the mobile device 300 is used along with the biometric data from the smartwatch 301, the vehicle 201 could potentially have no connection to the mobile device 300 at all. In this example, the vehicle 201 may be any sort of moving apparatus with variable accelerations, such as a motorcycle, bicycle, jet-ski, snow mobile, hang-glider, speed boat, truck, helicopter, or a carnival ride all could be moving apparatuses that might benefit from having mobile device 300 attached to it, which curates video based on the acceleration of that moving apparatus.

In the third example, where the vehicle 201 has a built-in camera, the vehicle 201 is capable of performing the video curation by itself, by combining the vehicle motion data with the video captured by the camera of the vehicle 201 and the biometric data from the smartwatch 301. The vehicle would only likely use a wireless radio to transfer the curated video to another device, but conceivably could play the curated video on the vehicle's display or digital interface.

Figure 2A:
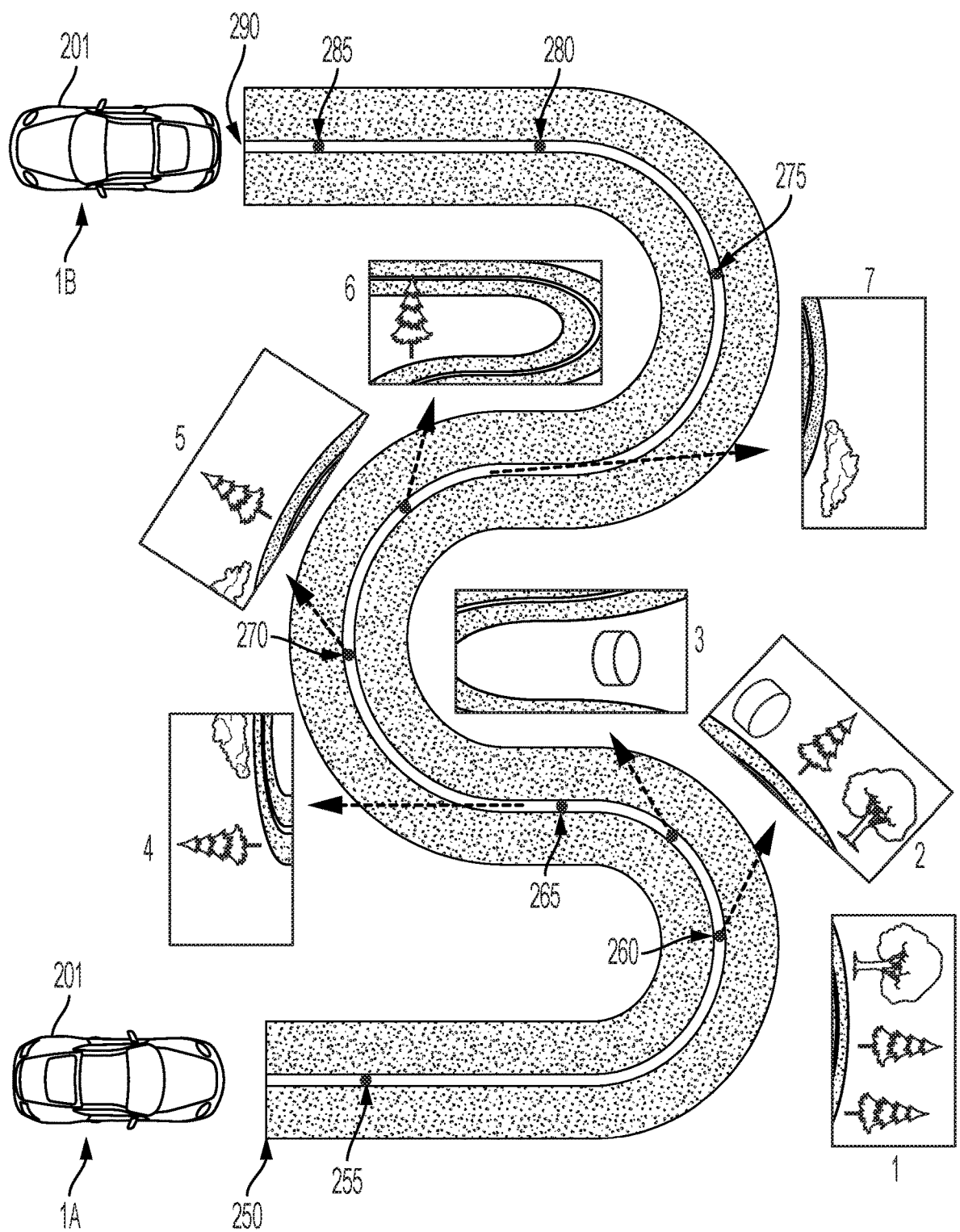
FIG. 2A is drawing of a vehicle moving along a road and collecting video and other information. It identifies the locations at which the curation software ultimately selects footage surrounding, and shows illustrative vignettes of the footage captured as the vehicle proceeds down the road.

Turning now to FIG. 2A, the vehicle 201 is shown driving along the road starting from position 250, turning left, right, then left again, before coming to rest at its final position 290. During this time, a camera on either vehicle 201 or the mobile device 300 records raw footage of the view from the front dashboard of the vehicle 201 and the biometric data is monitored and recorded by the smartwatch 301. The curation software in vehicle 201 or the mobile device 300 is configured to check for at least three conditions as the vehicle travels along the road. First, the software checks whether the acceleration of the vehicle (either positive or negative acceleration) is greater than a first absolute acceleration threshold. Second, the software checks whether the average acceleration of the vehicle is greater than a second absolute acceleration threshold (which is lower than the first threshold), while the steering wheel of the vehicle 201 has been turned at least one-half rotation (for example) in either direction. Third, the software checks whether the biometric data is greater than a pre-defined threshold (e.g., the heart rate itself exceeds a threshold value, or the acceleration of the heart rate exceeds a threshold value).

Figure 2B:
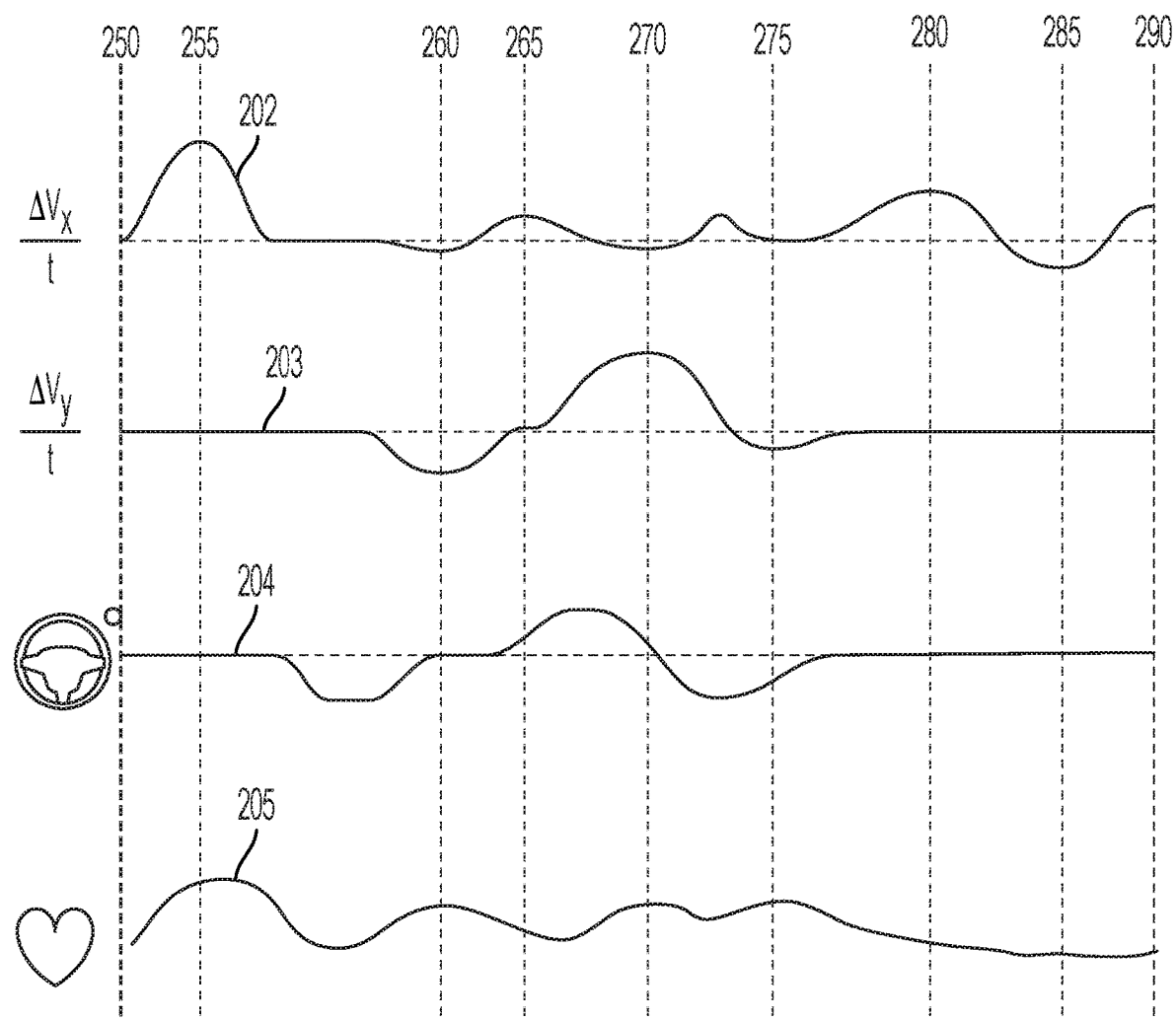
FIG. 2B depicts a three line (or curve) graph illustrating the longitudinal acceleration forces experienced by the vehicle, lateral acceleration forces experienced by the vehicle, and the steering wheel rotational position over time as the vehicle proceeds down the road in FIG. 2A.

The vehicle 201 accelerates, turns, decelerates, etc. along the course shown in FIG. 2A. FIG. 2B depicts the acceleration forces and the steering wheel rotation of the vehicle 201 during the drive from point 250 to point 290 shown in FIG. 2A. Plot 202 charts the forward and backward acceleration forces: positive values are forward acceleration, negative values are reverse acceleration. Plot 203 charts the left and right acceleration forces: positive values are left acceleration, negative values are right acceleration. Plot 204 charts the amount or degree the steering wheel is turned: positive values are left-turning distance from the center position, and negative values are right-turning distance from the center position. Plot 205 charts the heartrate of the driver during the drive from point 250 to point 290 shown in FIG. 2A.

The vehicle 201 experiences at least two exciting "moments" as it moves over the course of FIG. 2A, as adjudged by processor(s) operating according to the block diagrams depicted in FIGS. 4A-4D and 6, which figures will be described later. In particular, the moments occur at locations 260 and 270 along the course. For each moment at locations 260 and 270, the processor is configured to capture video, biometric and motion information before, during and after the moment. The periods before and after may be referred to as buffer periods. For example, for the moment at location 260, the processor capture video, biometric and motion information corresponding to clips or illustrations 1-4 in FIG. 2A. And, for the moment at location 270, the processor captures video, biometric and motion information corresponding to clips or illustrations 4-7 in FIG. 2A.

In the exemplary course shown in FIG. 2A, the vehicle only very temporarily satisfies the moment tagging criteria. In practice, the moment tagging could occur for an extended period of time. For example, if a driver tightly turned the vehicle in a "doughnut" shape while maintaining speed, the acceleration forces threshold and steering wheel rotation threshold could be satisfied indefinitely. Therefore, if a driver drove in a "doughnut" for ten full second, the moments selected might be the two moments before the "doughnut" turn started, the entire "doughnut" turn, and then the two moments after exiting the "doughnut" turn.

Figure 2C:
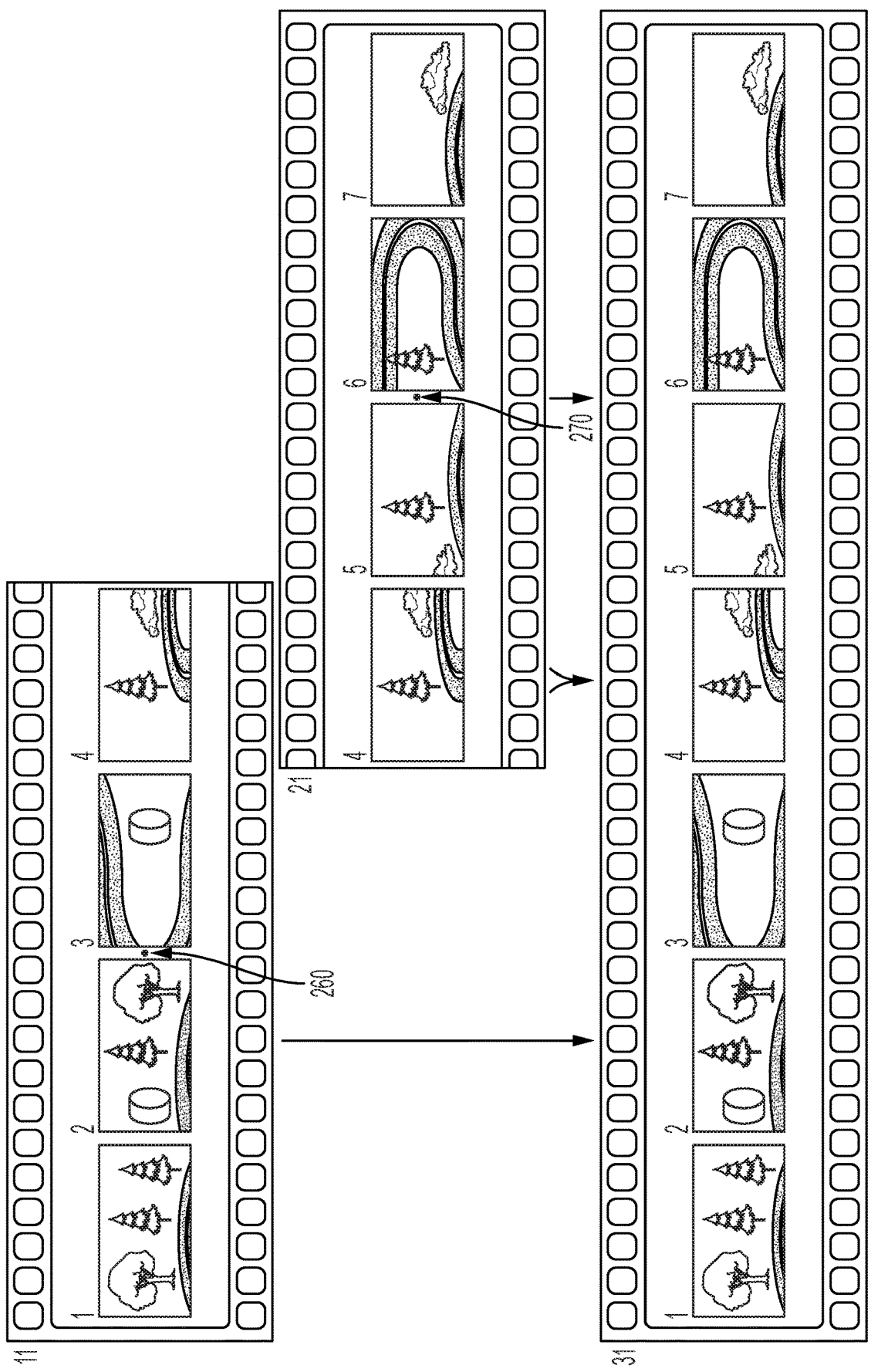
FIG. 2C depicts two selections of footage from the drive depicted in FIG. 2A that ultimately have duplicated segments. The figure also contains a single unified selection that removes the duplicate copy of the footage to create a continuous selection.

Once the drive is completed, the driver directs the software to perform post-processing, which is depicted at a high-level in FIG. 2C.

FIG. 2C is a depiction of the post-processing software at work. In FIG. 2A, moments were tagged at locations 260 and 270, as described above. In FIG. 2C, clips 1-4 are depicted in the first film strip 11 corresponding to the moment at location 260, whereas clips 4-7 are depicted in the second film strip 21 corresponding to the moment at location 270. Normally, these two strips would just be connected so that the last moment of the first strip 11 immediately leads into the first moment of the second strip 21. However, here both strips 11 and 21 include clip 4. Without proper curation, a curated video would contain clip 1, clip 2, clip 3, clip 4 twice, then clip 5, clip 6, and then clip 7. This however does not accurately represent the drive, as the vehicle 201 did not experience clip 4 twice. Therefore, the software edits one or both strips 11 and 12, removing one copy of the duplicate clip 4. Then, the software splices the strips 11 and 12 together, resulting in a continuous, brief, and exciting curated clip 31 of driving moments from a longer drive. Further details in connection with post processing will be described with reference to FIGS. 5 and 7.

Figure 3:
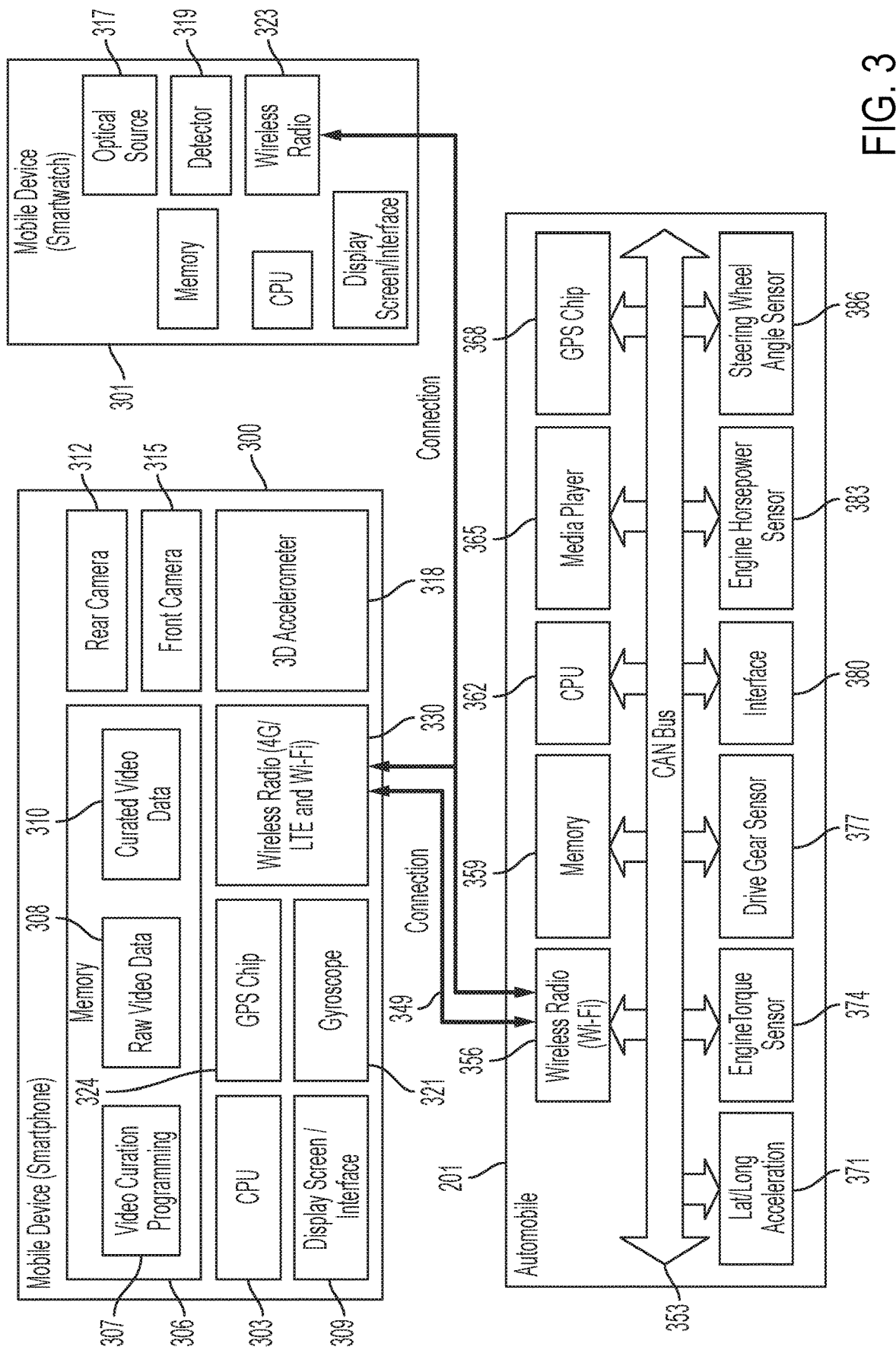
FIG. 3 is a functional block diagram of the video curation system. It shows a vehicle with multiple electronic control units (ECUs) that send measurements via a Wi-Fi radio to a mobile device to aid in video curation.

FIG. 3 is a functional block diagram of the video curation system. Generally, it depicts a mobile device 300 and a smartwatch 301 communicating with a vehicle 201 over radio communications, however, as noted above, the video curation system may include (i) only the mobile device 300 and smartwatch 301, or (ii) only the vehicle 201 and smartwatch 301. Alternatively, the smartwatch 301 may be omitted in its entirety.

The mobile device 300 includes a central processing unit (CPU) 303 formed of one or more processors and a main memory 306. The circuitry forming the CPU 303 may contain a single microprocessor. The circuitry forming the CPU 303 may contain a number of microprocessors for configuring the mobile device 300 as a multi-processor system, or the circuitry forming the CPU 303 may use a higher speed processing architecture. The main memory 306 in the example includes ROM, RAM and cache memory; although other memory devices may be added or substituted.

In operation, the main memory 306 stores at least portions of instructions and data for execution by the CPU 303. These instructions may include the video curation programming 307 which perform the video collection and curation. This programming can also be located in the vehicle memory 359, or possibly an off-site post-processing server, in alternative embodiments. The main memory 306 also stores the raw video data 308, captured during drives, as well as the curated video data 310 that is created after the post-processing. The CPU 303 and memory 306 may handle programs and files in a similar fashion for other functions of the mobile device 300.

The mobile device 300 also includes one or more input/output interfaces for communications, shown by way of example as a wireless radio 330. Although other wireless radio arrangements may be used, the example mobile device utilizes a wireless connection, such as a Wi-Fi type compatible with the particular iteration of Wi-Fi protocol utilized in communicating with the vehicle 201 as well as the smartwatch 301. The wireless connection may be a Bluetooth connection or a wired connection, for example.

The wireless radio 330 may be a high-speed modem, a Bluetooth transceiver, an Ethernet (optical, cable or wireless) card or any other appropriate data communications device. The physical communication link(s) from the mobile device 300 to the vehicle 201 as well as the smartwatch 301 may be optical, wired, or wireless (e.g., via satellite, cellular network, or Wi-Fi).

The mobile device 300 further includes an appropriate display screen 309 or the like, serving as a local user interface for configuration, programming or trouble-shooting purposes. The display screen 309 can be used to view the raw video data 308, as well as the curated video data 310.

The accelerometer 318 is an electronic device, such as an inertial measurement unit (IMU) that measures and reports, for example, the specific force on the mobile device 300. The accelerometer 318 measurements can be processed on the mobile device 300. The accelerometer 318 detects acceleration along the horizontal (X), vertical (Y), and depth or distance (Z) axes, which can be defined relative to the ground, the mobile device 300, or the vehicle 201.

The gyroscope 321 detects the rate of rotation around 3 axes (X, Y, and Z). This can therefore detect rotational rate through the horizontal (X), vertical (Y), and depth or distance (Z) axes, which can also be defined relative to the ground, the mobile device 300, or the vehicle 201.

The GPS chip 324 is a chip that uses the Global Positioning System (GPS) to track the mobile device 300 and determine its location. This data can be stored in the mobile device 300 memory 306 and potentially be used by the video curation programming 307.

The mobile device 300 also has a front camera 315 and rear camera 312. This example embodiment has two cameras, but only one camera is needed to capture footage. The second camera can either serve as a backup, or capture different footage for the curation programming 307.

Turning now to the features of the smartwatch 301, as is described by Apple, the smartwatch 301 includes an optical heart sensor which relies upon photoplethysmography. This technology is based on the fact that blood is red because it reflects red light and absorbs green light. According to one exemplary embodiment, the smartwatch 301 uses green LED lights (generally depicted as optical source 317) paired with light-sensitive photodiodes (generally depicted as detector 319) to detect the amount of blood flowing through the user's wrist at any given moment. When a heart beats, the blood flow in the wrist—and the green light absorption—is greater. Between beats, the blood flow is less. By flashing the optical source 317 hundreds of times per second, the CPU of the smartwatch 301 is configured to calculate the number of times the heart beats each minute, i.e., the heart rate. The optical heart sensor can also use infrared light or rely on a pressure sensor.

The smartwatch 301 includes a wireless radio 323, like the wireless radio 330, that is configured to communicate the heart rate related data to the wireless radio 356 of the vehicle (among other devices). Alternatively, the smartwatch 301 may communicate the heart rate related data to the mobile device 300, which, in turn, communicates the heart rate related data to the wireless radio 356 of the vehicle. As another alternative, the smartwatch 301 may communicate the heart rate related data to (only) the mobile device 300. The smartwatch 301 may be an Apple Watch, for example, or any other type of smartwatch that is configured to collect biometric data. Further details of the smartwatch 301 may be found in U.S. Patent App. Pub. No. 2017/0340209, which is incorporated by reference herein in its entirety and for all purposes.

As an alternative to the smartwatch, the optical heart sensor may be embedded within the steering wheel of the vehicle. It should be understood that the optical heart sensor may vary from that which is shown and described. The heart rate sensor may be any conventional heart rate sensor that is known to those skilled in the art.

Turning now to the components of the vehicle 201, the vehicle 201 includes a central processing unit (CPU) 362 formed of one or more processors and a main memory 359. The circuitry forming the CPU 362 may contain a single microprocessor, or the circuitry forming the CPU 362 may contain a number of microprocessors for configuring the vehicle 201 as a multi-processor system. The main memory 359 in the example includes ROM, RAM and cache memory; although other memory devices may be added or substituted.

In operation, the main memory 359 stores at least portions of instructions and data for execution by the CPU 362. In this embodiment, these instructions do not include the video curation programming 307 which perform the video collection and curation, but this programming could be located in the vehicle memory 359 in alternative embodiments. The main memory 359 could also store the raw video data 308, captured during drives, as well as the curated video data 310 that is created after the post-processing, depending on the embodiment. The CPU 362 and memory 359 may handle programs and files in a similar fashion for other functions of the vehicle 201.

The vehicle 201 also includes one or more input/output interfaces for communications, shown by way of example as a wireless radio 356. Although other wireless radio arrangements may be used, the vehicle 201 utilizes a Wi-Fi type compatible with the particular iteration of Wi-Fi protocol utilized in communicating with the mobile device 300 and/or the smartwatch 301. The wireless radio 356 may be a high-speed modem, a Bluetooth transceiver, an Ethernet (optical, cable or wireless) card or any other appropriate data communications device. The physical communication link(s) from the vehicle 201 to the mobile device 300 and smartwatch 301 may be optical, wired, or wireless (e.g., via satellite, cellular network, or Wi-Fi).

The vehicle 201 further includes an appropriate display interface 380 or the like, serving as a local user interface for configuration, programming or trouble-shooting purposes. The display interface 380 can be used to view the raw video data 308, as well as the curated or final video data 310, in embodiments where the display interface 380 is a screen. The display interface 380 in the vehicle may also be configured for modifying the video, for example, by changing (e.g., adding, deleting, moving, re-ordering, etc.) the tag points or changing the length of the various film strips 11, 21 that comprise the video. The mobile device 300 may also include such a mechanism for modifying the video.

The Controller Area Network (CAN) bus 353 operates by allowing systems connected to the bus, such as the electronic control units (ECUs), to send messages through the bus to other ECUs. Alternatively, an ECU can broadcast data over the bus 353. ECUs might include the vehicle's CPU 362, the engine torque sensor 374, and the accelerometer 371.

The vehicle accelerometer 371 is an electronic device, such as an inertial measurement unit (IMU) that measures and reports, for example, the vehicle's specific acceleration force. The accelerometer 371 measurements can be processed on the vehicle's CPU 362. The accelerometer 371 detects acceleration along the X, Y and/or Z axes, which can be defined relative to the ground or the vehicle 201.

The engine torque sensor 374 measures and records the torque of the engine. The engine torque sensor 374 can then send its readings to the vehicle CPU 362, or to the mobile device 300 via the wireless radio 356. The engine horsepower sensor 383 may additionally capture the revolutions per minute (RPM) of the engine's drive shaft.

The drive gear sensor 377 tracks the vehicle's current gear. The drive gear sensor 377 can then send its readings to the vehicle CPU 362, or to the mobile device 300 via the wireless radio 356.

The GPS chip 368 is a chip that uses the Global Positioning System (GPS) to track the vehicle 201 and determine its location. This data can be stored in the vehicle memory 359 or the mobile device memory 306 and potentially be used by the video curation programming 307.

The media player 365 is integrated with the interface 380 in this embodiment, and reports via the CAN bus 353 the current music track played by the driver. This information can be saved in either memory 306 or 359 and used by the video curation programming 307.

The steering wheel angle sensor 386 measures the amount or degree of rotation of the steering wheel. The sensor 386 can measure direction and magnitude of the turning, or just the magnitude. In this embodiment the sensor 386 measures both. This information can be reported via the CAN bus 353 to the vehicle CPU 362 and memory 359, or to the mobile device 300 via the wireless radio 356.

Figure 4A:
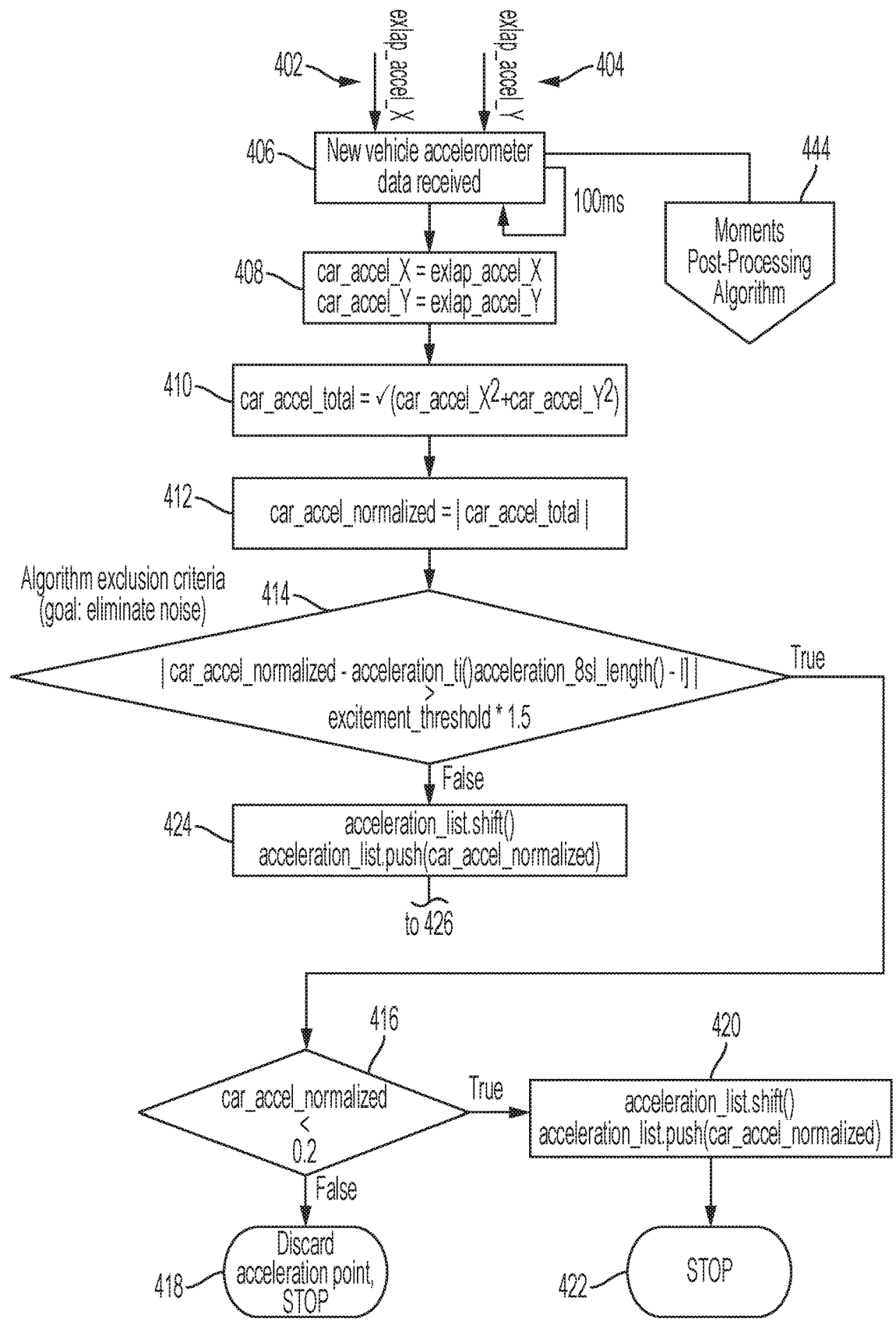
FIGS. 4A-4D depict flowcharts of the tagging portion of the video curation process, as performed using the vehicle and smartwatch sensors.
Figure 4A:
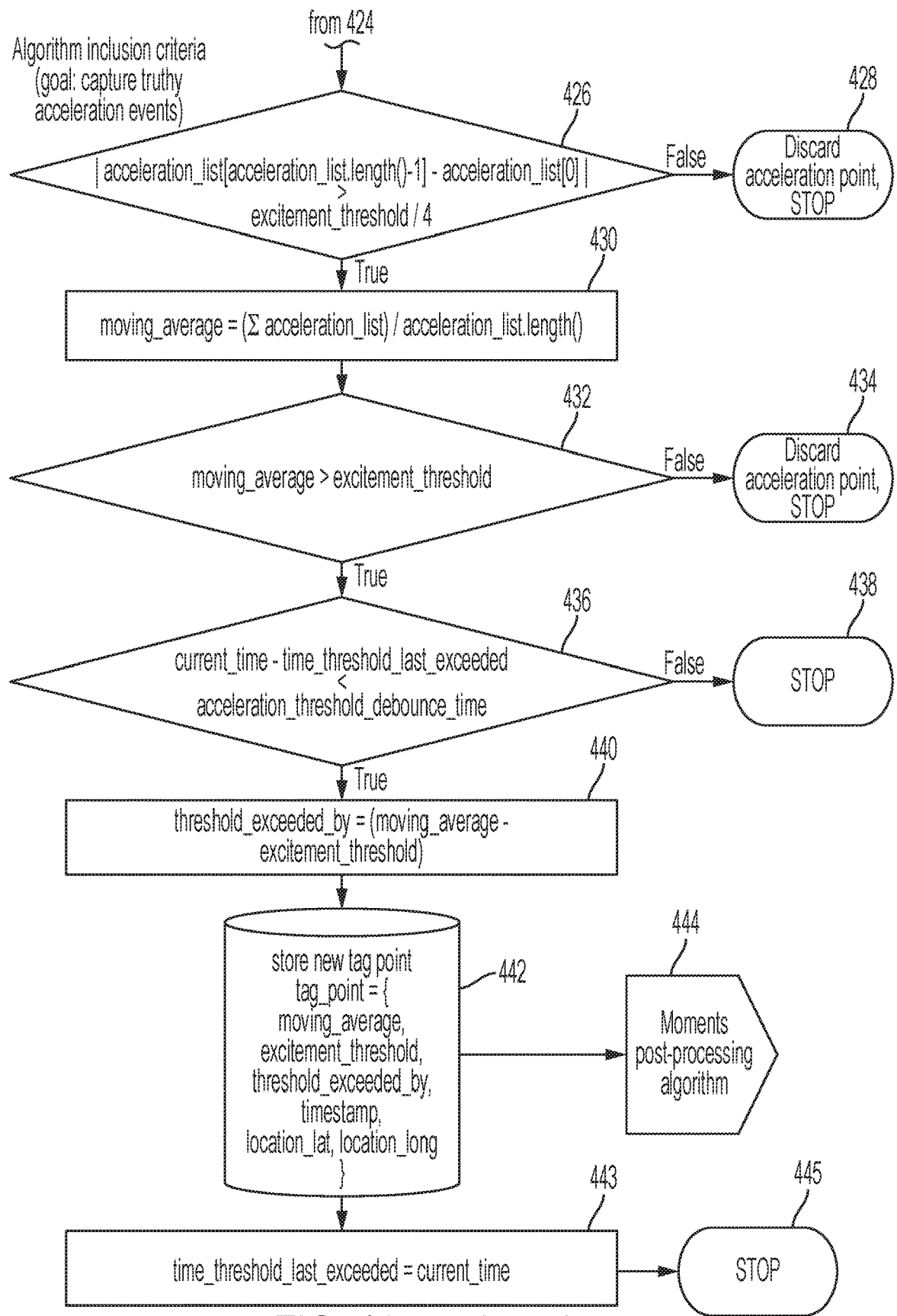

FIGS. 4A-4D are flowcharts depicting how, in an embodiment where the vehicle's sensors are utilized, specific moments in a video are tagged to be later used in curation and post-processing. FIG. 4A depicts the process for tagging moments based entirely on acceleration measurements. The inputs for this process are the acceleration forces sensed through the X axis 402, and the acceleration forces sensed through the Y axis 404. These forces are sensed by the vehicle's accelerometer 371, as noted above. These forces are sensed in operation 406 periodically, such as every 100 milliseconds. These forces are time-stamped and outputted to the post-processing algorithm 444 to be superimposed in real-time on the final video, as will be described with reference to operation 503. Operation 408 sets these sensed values into two stored variables: vehicle acceleration X for X-axis acceleration forces, and vehicle acceleration Y for Y-axis acceleration forces. Operation 410 applies the Pythagorean theorem to these two vectors to create a resultant vector. The absolute value of the resultant vector is then taken in operation 412, so that the resultant vector representing the vehicle's acceleration is always positive.

Operation 414 is an exclusionary operation, designed to eliminate noisy data. Here, the positive acceleration vector (car_accel_normalized) has the previous positive acceleration vector (acceleration_list.length( )−1) value subtracted from it, and the result is normalized. This captures the change in acceleration, and expresses it as a positive value. This change in acceleration value is then compared to an "excitement threshold" value, multiplied by 1.5. The excitement threshold is a value set by the user, and has no units. This "excitement threshold" value multiplied by 1.5 could be called an acceleration excitement threshold value If, in operation 414, the change in acceleration exceeded the acceleration excitement threshold value, then that change in acceleration is compared to the quantity 0.2 in operation 416. This is to confirm that the acceleration is material, even if the change in acceleration is material. If the acceleration is not material, operation 418 occurs. During operation 418, the list of acceleration points is wiped out, and the process returns to operation 406. If the acceleration is material, then the acceleration vector is added to the list of acceleration vectors, and the acceleration vector becomes the previous acceleration vector used in operation 414. After this, the process stops, and returns to operation 406.

If, in operation 414, the change in acceleration did not exceed the acceleration excitement threshold value, then the acceleration vector is added to the list of acceleration vectors in operation 424. This indicates that the acceleration cycle has completed, and in a typical scenario the vehicle is near or at cruising speed. Therefore, since the vehicle acceleration has completed, the flowchart then determines whether the acceleration was overall worthy of curation. In operation 426, the first acceleration vector is subtracted from the last acceleration vector, and then the absolute value of that difference is taken. If this absolute difference in acceleration vectors exceeds the excitement threshold divided by four, this indicates that the difference in acceleration was material, and could be included. If the absolute difference in acceleration vectors does not exceed the excitement threshold divided by four, this indicates that the overall acceleration event did not produce a major change in acceleration, and so in operation 428 the list of acceleration points is wiped out, and the process returns to operation 406.

If the result of operation 426 is that the absolute difference in acceleration vectors exceeds the excitement threshold divided by four, then the moving average is calculated in operation 430. This moving average is the sum of all acceleration vectors captured, divided by the number of acceleration vectors. This moving average is then compared to the excitement threshold in operation 432. If the moving average of acceleration vectors is less than the excitement threshold, then the average acceleration was not exciting enough, and operation 434 has the list of acceleration points wiped out, returning the process to operation 406.

If this moving average does exceed the excitement threshold, then the series of acceleration vectors has been deemed "exciting" enough. Operation 436 then determines whether a tagged moment has occurred too recently. This operation utilizes a debounce function. Debounce functions limit the rate at which another operation can occur within a debounce time. If the difference in the current time and the time an exciting moment last occurred does not exceed the debounce time, then the moment is too close, and for now is not added. Operation 438 does not wipe out the list of acceleration points, and merely returns the process to operation 406. If the difference in the current time and the time an exciting moment last occurred does exceed the debounce time, then the moment is sufficiently far from the last tagged moment, and the process proceeds to saving the tagged moment.

Operation 440 involves calculating how much the excitement threshold was exceeded by, which is simply subtracting the excitement threshold from the moving average.

With the various values calculated, and a determination made, the values are ready for storing in the memory. Operation 442 stores a tag point, which includes the moving average, the excitement threshold, how much the excitement threshold was exceeded by the moving average, a timestamp indicated when the tag point occurred, and the latitude and longitude of the vehicle when the tag point was generated in a database. This tag point database is used by the post-processing algorithm 444. Next, operation 443 sets the time an exciting moment last occurred to the current time. At this point, operation 445 returns the process to operation 406, unless the drive has been completed. In that case, the process proceeds to post-processing, described in FIG. 5.

Figure 4B:
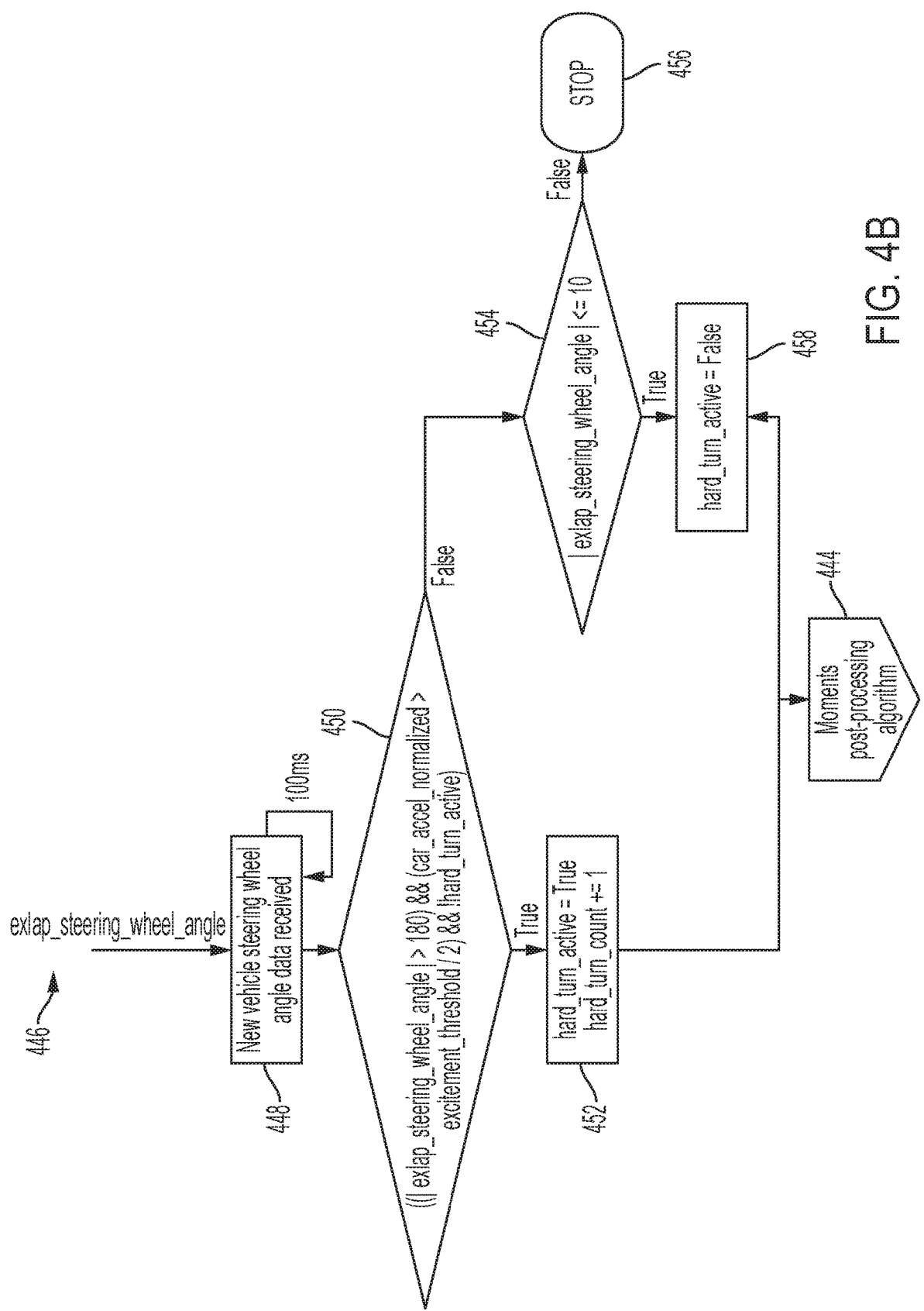

FIG. 4B depicts the process for collecting hard turn counts based on steering wheel angle. This process also makes use of the positive acceleration vector created every 100 ms in operation 412 of FIG. 4A. The input for this process beyond the positive acceleration vector from operation 412 is the angle of the steering wheel 446. This angle is sensed by the vehicle's built-in steering wheel angle sensor 386. This angle is sensed in operation 448 periodically, such as every 100 milliseconds. Operation 450 is an exclusionary operation, designed to eliminate noisy data. Here, the following questions are evaluated: Is the steering wheel's absolute angle beyond 180 degrees? Is the positive acceleration vector from operation 412 greater than half of the excitement threshold value? Is the vehicle not currently considered to be engaging in a "hard turn"? If all three of those statements are true, then the process moves to operation 452. In this operation, the vehicle is set to be considered to be engaging in a "hard turn", and the number of hard turns is incremented, and that information is passed to the post-processing algorithm 444 in operation 452.

If one of the statements from operation 450 is not true (i.e., false), then the vehicle is either not performing a hard turn, or was performing a hard turn 100 milliseconds ago. To check, operation 454 determines whether the steering wheel's absolute angle is less than or equal to 10 degrees. If it is not, then the vehicle is still turning hard, and the process exits in operation 456 and returns to operation 448. If the steering wheel's absolute angle is less than or equal to 10 degrees, then the vehicle is not considered to be engaging in a "hard turn" in operation 458. This information is passed to the post-processing algorithm 444. The process then moves back to operation 448, ready to check for and count the next "hard turn" the driver might make.

Figure 4C:
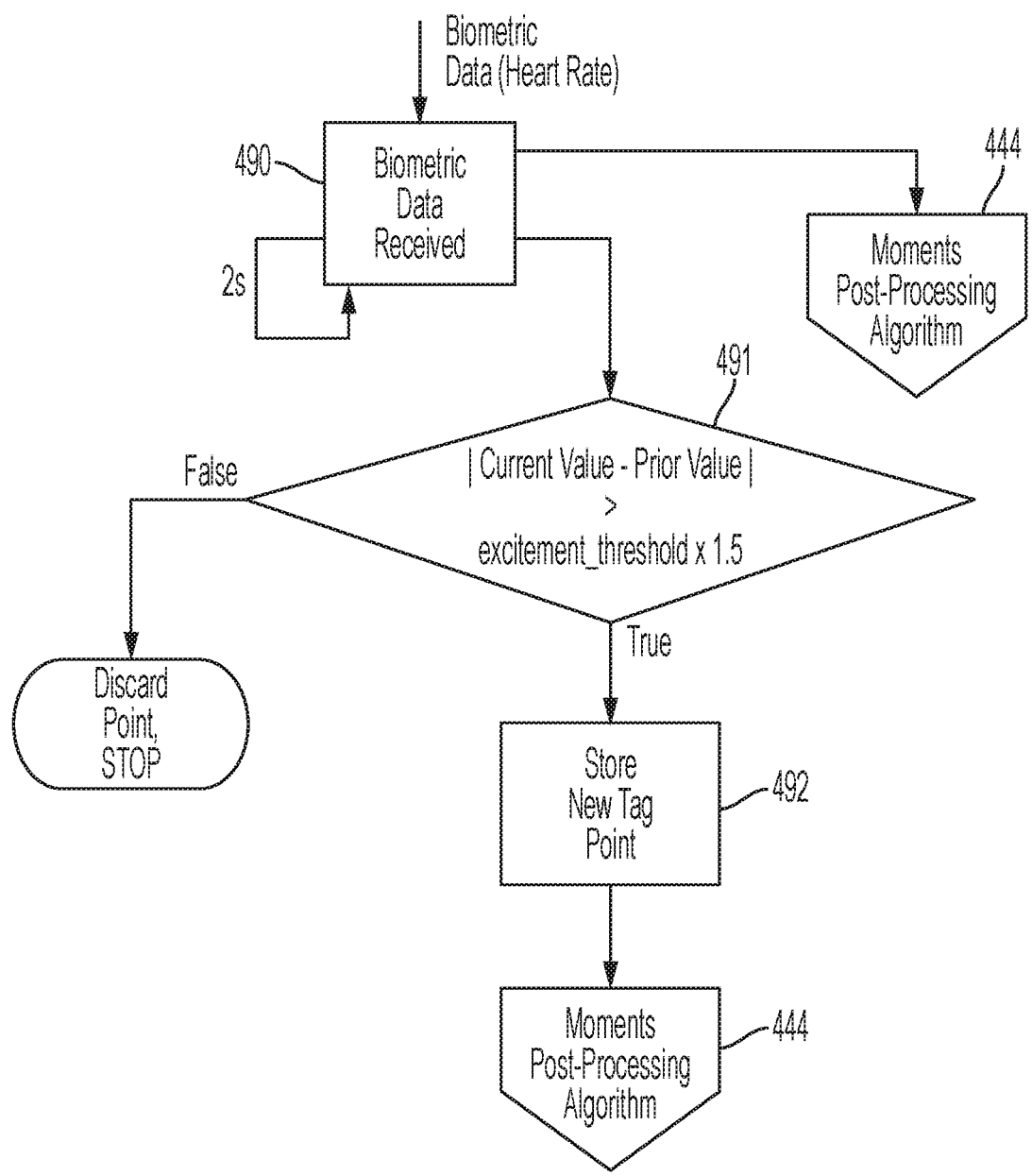

FIG. 4C depicts the process for tagging moments based entirely on biometric data. The input for this process is the biometric data (e.g., heart rate or blood pressure of the driver) transmitted by the smart watch 301 to either the vehicle CPU 362 (depending upon the arrangement of the system). This biometric data is received in operation 490 periodically, such as every 2 seconds. This biometric data is time-stamped and outputted to the post-processing algorithm 444 to be superimposed in real-time on the final video, as will be described with reference to operation 503. This data is also passed to the post-processing algorithm in operation 483.

Operation 491 is an exclusionary operation, designed to eliminate noisy data. Here, the current biometric data value has the previous biometric data value subtracted from it, and the result is normalized. This captures the change in biometric data value, and expresses it as a positive value. This change in biometric data value is then compared to an "excitement threshold" value, multiplied by 1.5. The excitement threshold is a value set by the user or original equipment manufacturer, and has no units. This "excitement threshold" value multiplied by 1.5 could be called an biometric data excitement threshold value.

If the result of operation 491 is true, then the driver is considered to be engaging in an exciting moment and the biometric data is timestamped and a new tag point is stored at operation 492, and the new tag point is forwarded to the post-processing algorithm 444.

If the result from operation 491 is not true (i.e., false), then the driver is not considered to be engaging in an exciting moment, or is beginning to relax. The process then moves back to operation 490, ready to check for the next exciting driving moment as adjudged by biometric data.

Alternatively, operation 491 can be simplified. For example, the heart rate from operation 490 can simply be compared against a pre-determined heart rate value, such as 170 beats per minute (bpm) (or, more generally 220 bpm minus the driver's age), and, if the driver's heart rate exceeds the pre-determined value, then the result from the operation 491 will be 'true.' If the heart rate does not exceed the pre-determined value, then the result from the operation 491 will be 'false,' which indicates that, when using the 'predetermined threshold' approach, if the drivers heart rate is below this threshold, there will not be a tag point generated.

Figure 4D:
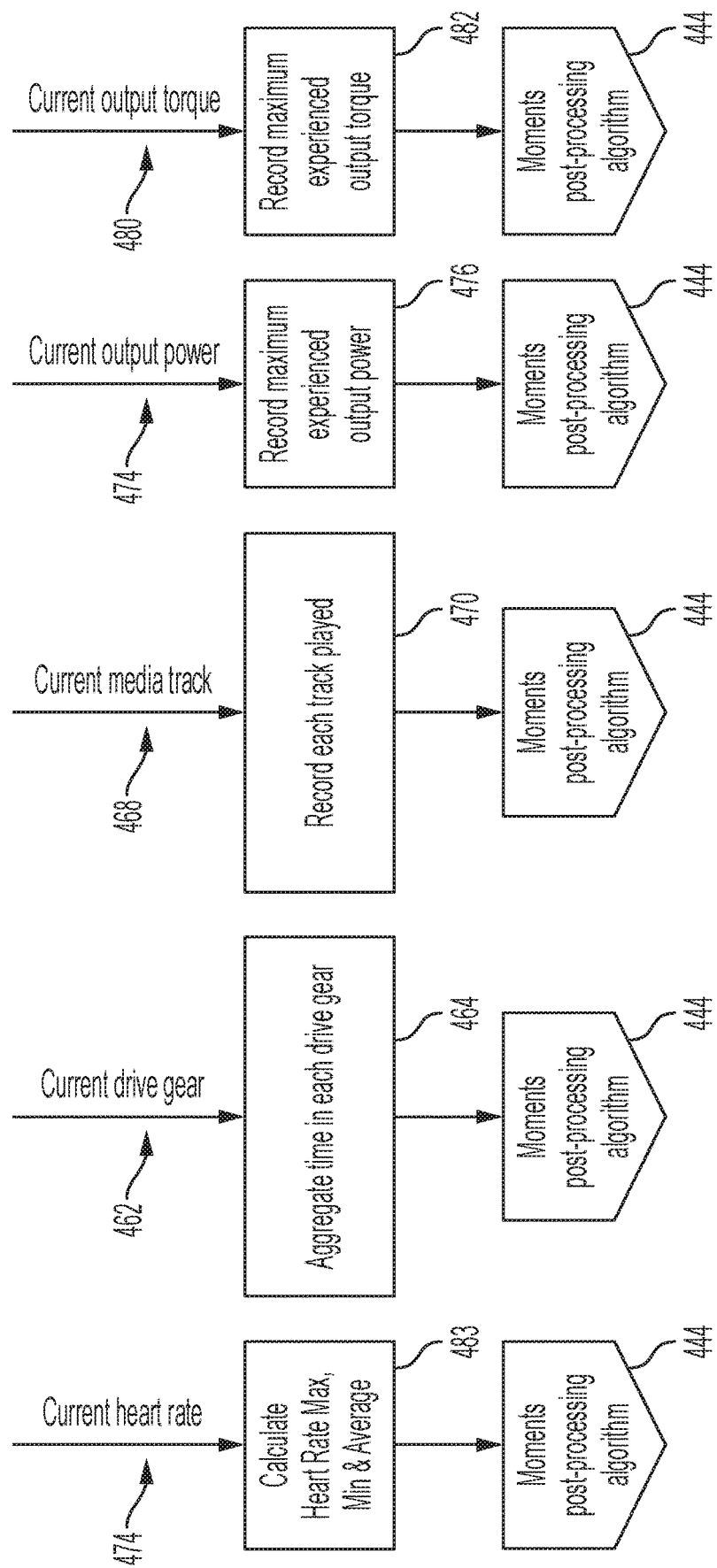

FIG. 4D depicts ancillary information that is inputted into post-processing algorithm 444. More particularly, the current drive gear 462 from the drive gear sensor 377 is put into an aggregation in operation 464, so that the post-processing algorithm 444 can have a count of the total time each drive gear was used. Additionally, the current music track 468 from the media player 365 is put into a list in operation 470, so that the post-processing algorithm 444 can have a list of each music track played. Further, the current output power 474 from the engine horsepower sensor 383 has the maximum recorded value selected in operation 476, so that the post-processing algorithm 444 can have the maximum experienced output power. The current output torque 480 from the engine torque sensor 374 has the maximum recorded value selected in operation 482, so that the post-processing algorithm 444 can have the maximum experienced output torque. Finally, in operation 483, the driver's heart rate data provided by the smartwatch 301 is time-stamped and provided to the post-processing algorithm 444. And, in operation 483, the maximum heart rate, minimum heart rate and/or average heart rate may be calculated and provided to the post-processing algorithm 444.

Figure 5:
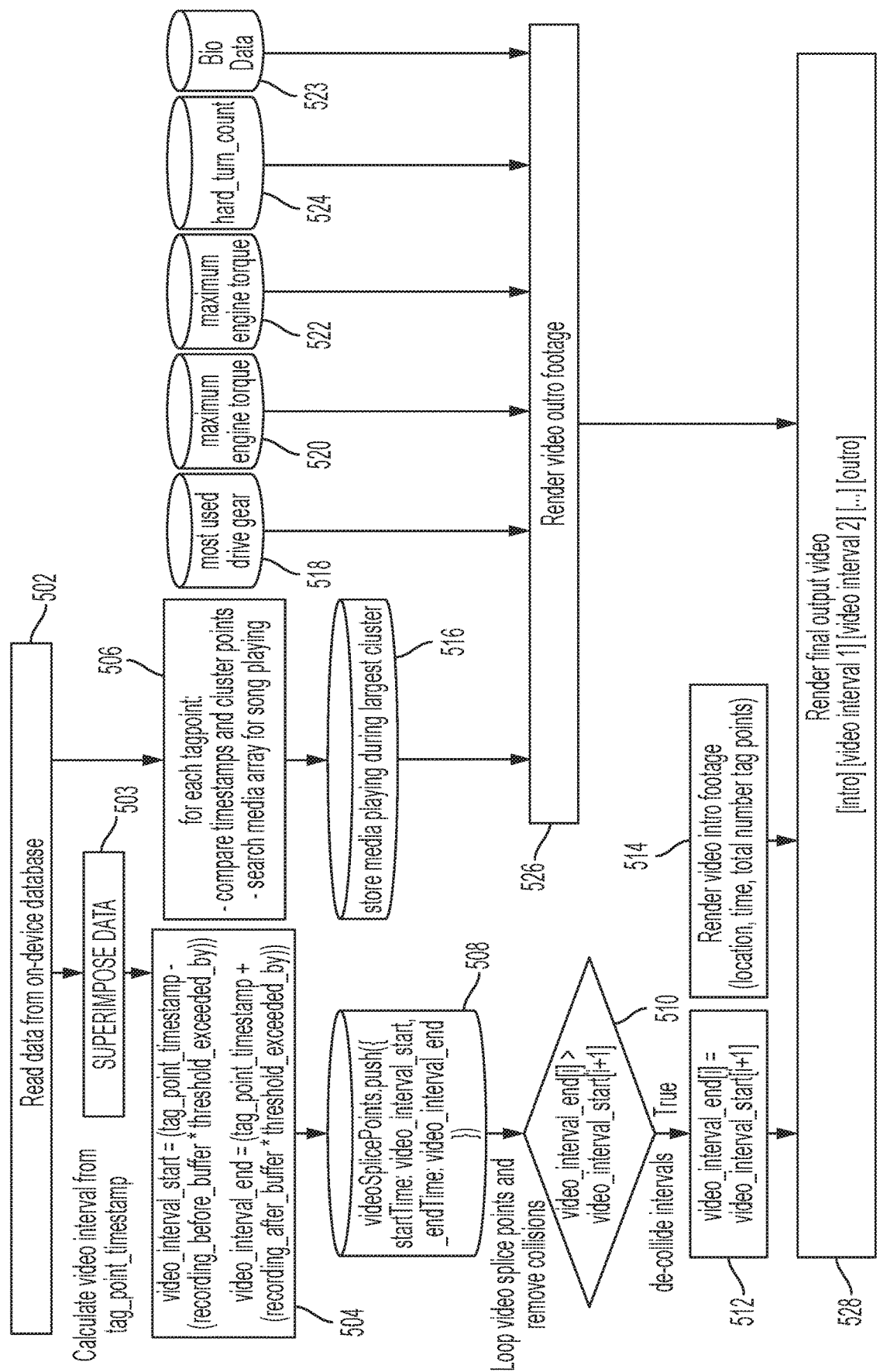
FIG. 5 is a flowchart of the post-processing portion of the video curation process, as performed using the vehicle sensor and biometric tags.

FIG. 5 is a flowchart depicting how, in an embodiment where the vehicle's sensors were used, specific moments from a video that were tagged to be used in curation are post-processed. Operation 502 reads the data from the database of tag points, which is populated in operation 442 of FIG. 4A and/or operation 492 in FIG. 4C. This operation also reads in the entire raw video file, to be curated using the tag points from operations 442 and 492.

At operation 503, the real-time motion-related data (e.g., vehicle speed, acceleration, and steering wheel angle) collected at steps 446 and 448 and/or real-time biometric data (e.g., heart rate) collected at step 490 are superimposed onto the video footage. Alternatively, the operation 503 may be completed immediately prior to step 528 such that the real-time motion-related data and/or real-time biometric data is only superimposed on the final clips of the video. The real-time motion-related data and/or real-time biometric data can be placed at the appropriate points within the video using the time-stamp information as a guide.

Then, in operation 504, the timestamp of a tag point is taken. This timestamp has a start and finish timestamp calculated based on the timestamp. The start timestamp is a buffer period of time (in this embodiment 2500 milliseconds) multiplied by how much the excitement threshold was exceeded by the moving average, earlier than the tag point time stamp. So, if the amount the excitement threshold was exceeded by the moving average is two, then the start timestamp is 5000 milliseconds before the tag point time stamp (2.0×2500 milliseconds). Equivalently, the end timestamp is the buffer period of time multiplied by how much the excitement threshold was exceeded by the moving average, later than the tag point time stamp. If the amount the excitement threshold was exceeded by the moving average is two, then the final span of time is 10000 milliseconds:5000 milliseconds before the tag point time stamp, and 5000 milliseconds after the tag point time stamp. This range is then pushed into a list in operation 508. Operations 504 and 508 are repeated for every tag point. The time periods and values provided herein are provided for purposes of example, and should not be construed as limiting.

In operation 510, each time range is compared to the other time ranges. If a time range's end is after the next time range's beginning, the time range's end is set to be equal to the next time ranges beginning in operation 512. This de-collides the ranges of time, and removes overlaps. Operations 510 and 512 generally depict de-collision of timespans. While edge cases exist (e.g. three timespans, each three seconds long, each starting one second after the other) that are not fully covered by these brief explanations of de-collision, conventional algorithms and methods may be used by a person of ordinary skill in the art to sufficiently detect overlapping spans, remove the overlaps, and create a smooth continuum of spans with no collisions. The intervals are then used to select corresponding segments of footage from the raw video file, and these segments are used in operation 528.

In operation 514, video intro footage is rendered. This footage is to be placed ahead of the footage from operation 512 by operation 528. The intro footage contains metadata about the drive such as location, time, the total number of tag points, and possibly branding and copyright information.

Operation 506 descends from operation 502. Here, the tag points are used, as well as the media list passed in operation 470. The media list timespans are checked against the tag points, and if a media track is playing during the largest cluster of tag points, that media track is stored in operation 516.

Operation 526 renders video outro footage. This footage is to be placed behind the footage from operation 512 by operation 528. The outro footage uses the media track from operation 516 as its sound track. The outro footage also uses the most used gear drive 518, passed from operation 466 to display in the outro. The outro footage additionally uses the maximum engine power 520, passed from operation 476 to display in the outro. Further, the outro footage uses the maximum engine torque 522, passed from operation 482 to display in the outro. Further, the outro footage uses the biometric data (such as the maximum, minimum and average heart rate), passed from operation 483 to display in the outro. Finally, the outro footage uses the hard turn count, passed from operation 452 or 458 to display in the outro. The outro might contain branding and copyright information.

Operation 528 is the final operation, which takes the intro footage from operation 514, appends the drive footage including data (motion and biometric) from operation 512 sequentially, and then appends the outro footage from operation 526. This operation creates a final contiguous video file, which is then stored in a database, and optionally displayed on a video display. The motion-related data (e.g., vehicle speed, acceleration, and steering wheel angle) and biometric data (e.g., heart rate) are displayed in real-time in the video, such that a viewer of the video can identify the current vehicle speed and heart rate, for example, at any point during the drive footage.

Figure 6:
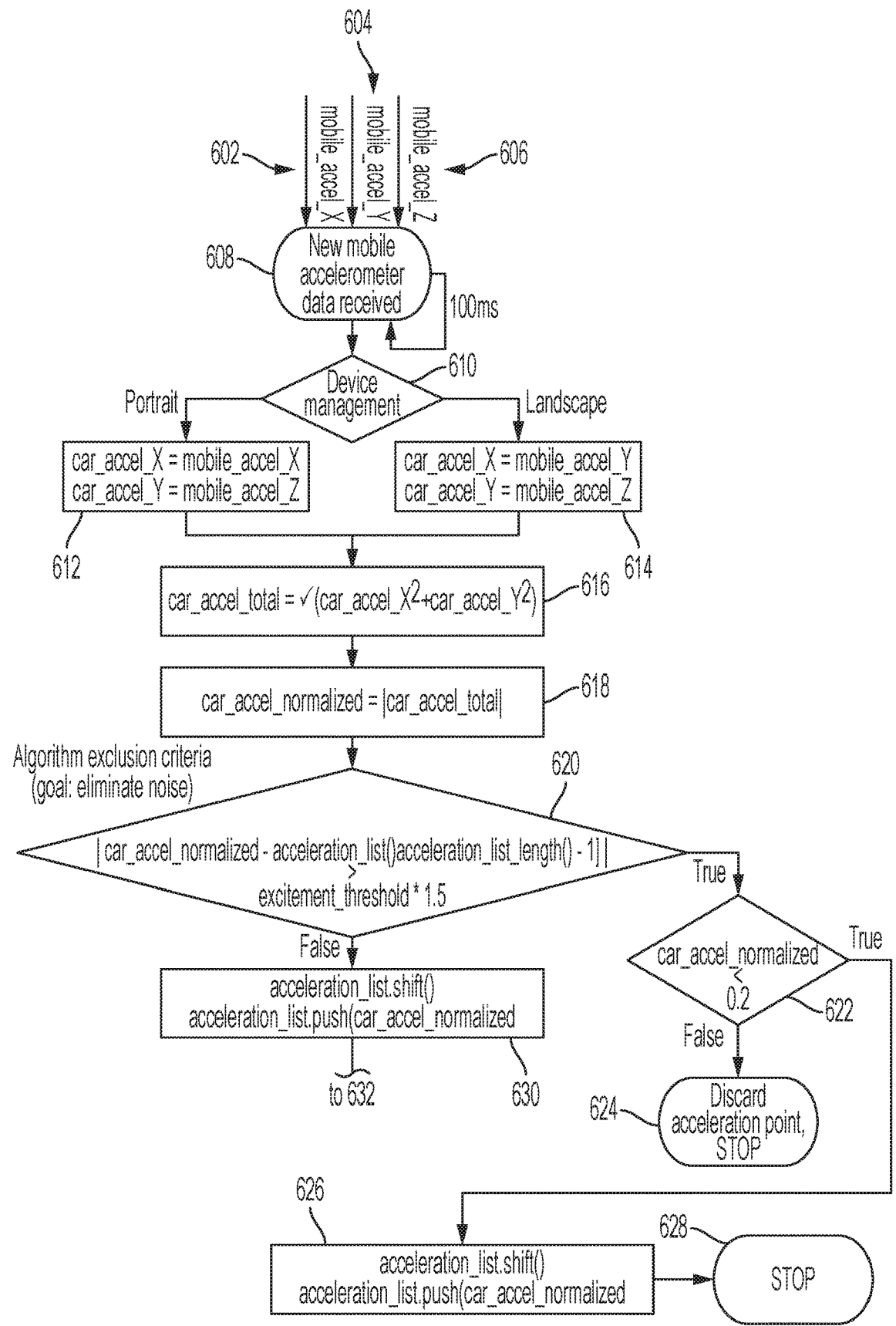
FIG. 6 is a flowchart of the tagging portion of the video curation process, as performed using the mobile device sensors.
Figure 6:
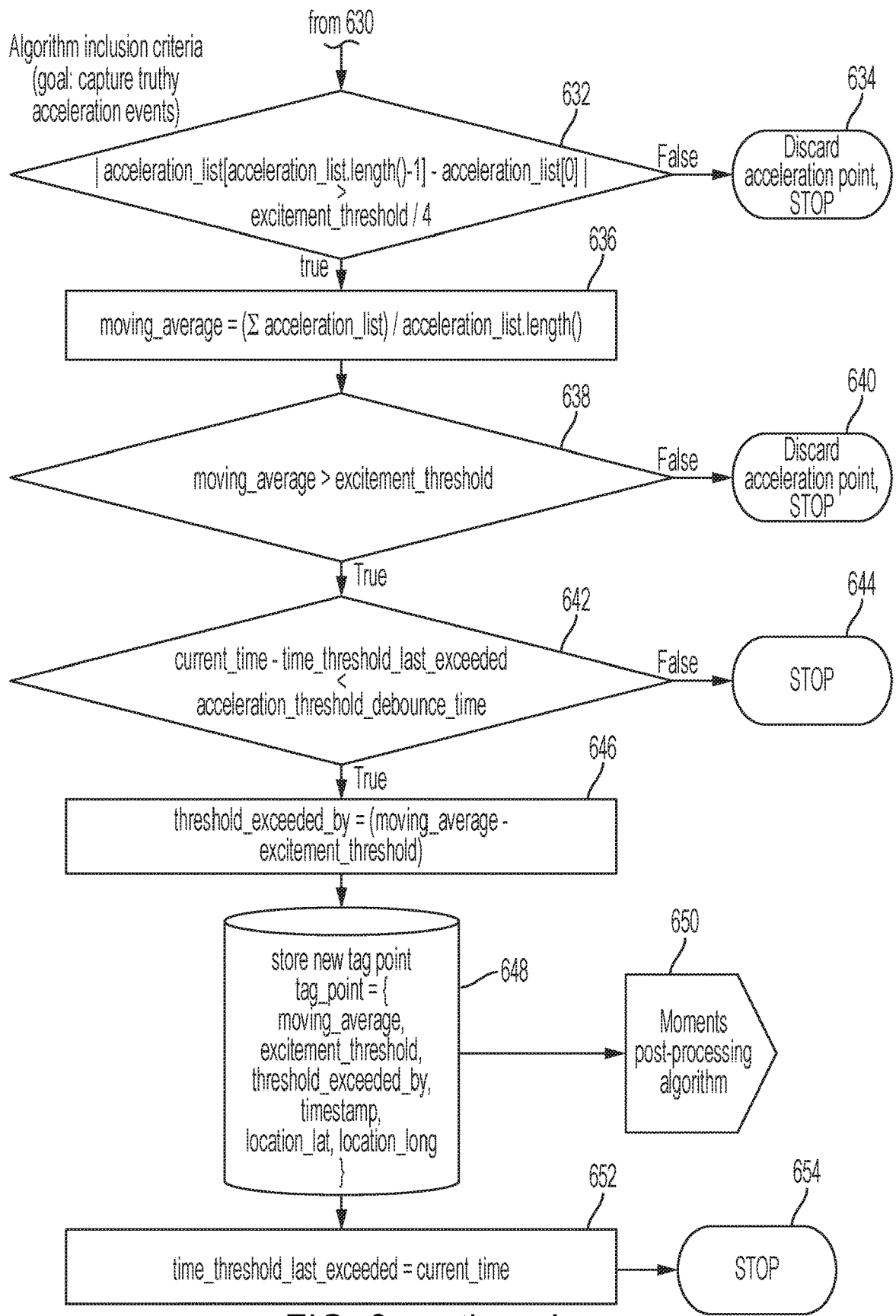

FIG. 6 is a flowchart depicting how, in an embodiment where the sensors of the mobile device 300 are used in lieu of sensors on the vehicle, specific moments in a video are tagged to be later used in curation and post-processing. The inputs for this process are the acceleration forces sensed through the X axis 602, the acceleration forces sensed through the Y axis 604, the acceleration forces sensed through the Z axis 606, and the biometric data transmitted by the smartwatch 301.

The three aforementioned acceleration forces are sensed by the mobile device's built-in 3D accelerometer 318. These forces are sensed in operation 608 periodically, such as every 100 milliseconds. Operation 610 assesses the orientation of the mobile device. If the mobile device 300 appears to be in a vertical, or "portrait" orientation, then operation 612 is selected, which sets these sensed values into two stored variables: mobile device acceleration X for X-axis acceleration forces, and mobile device acceleration Z for Y-axis acceleration forces. Alternatively, if the mobile device appears to be in a horizontal, or "landscape" orientation, the operation 614 is selected, which sets these sensed values into two stored variables: mobile device acceleration Y for X-axis acceleration forces, and mobile device acceleration Z for Y-axis acceleration forces.

Operation 616 applies the Pythagorean theorem to these two vectors to create a resultant vector. The absolute value of the resultant vector is then taken in operation 618, so that the resultant vector representing the mobile device's acceleration is always positive.

Operation 620 is an exclusionary operation, designed to eliminate noisy data. Here, the positive acceleration vector (car_accel_normalized) has the previous positive acceleration vector (acceleration_list.length( )−1) value subtracted from it, and the result is normalized. This captures the change in acceleration, and expresses it as a positive value. This change in acceleration value is then compared to an "excitement threshold" value, multiplied by 1.5. The excitement threshold is a value set by the user, and has no units. This "excitement threshold" value multiplied by 1.5 could be called an acceleration excitement threshold value If, in operation 620, the change in acceleration exceeded the acceleration excitement threshold value, then that change in acceleration is compared to 0.2 in operation 622. This is to confirm that the acceleration is material, even if the change in acceleration is material. If the acceleration is not material, operation 624 occurs. In operation 624, the list of acceleration points is wiped out, and the process returns to operation 608. If the acceleration is material, then the acceleration vector is added to the list of acceleration vectors, and the acceleration vector becomes the previous acceleration vector used in operation 620. After this, the process stops, and returns to operation 608.

If, in operation 620, the change in acceleration did not exceed the acceleration excitement threshold value, then the acceleration vector is added to the list of acceleration vectors in operation 630. This indicates that the acceleration cycle has completed, and in a typical scenario the vehicle the mobile device is within is near or at cruising speed. Therefore, since the vehicle acceleration has completed, the flowchart then determines whether the acceleration was overall worthy of curation. In operation 632, the first acceleration vector is subtracted from the last acceleration vector, and then the absolute value of that difference is taken. If this absolute difference in acceleration vectors exceeds the excitement threshold divided by four, this indicates that the difference in acceleration was material, and could be included. If the absolute difference in acceleration vectors does not exceed the excitement threshold divided by four, this indicates that the overall acceleration event did not produce a major change in acceleration, and so in operation 634 the list of acceleration points is wiped out, and the process returns to operation 608.

If the result of operation 632 is that the absolute difference in acceleration vectors exceeds the excitement threshold divided by four, then in the moving average is calculated in operation 636. This moving average is the sum of all acceleration vectors captured, divided by the number of acceleration vectors. This moving average is then compared to the excitement threshold in operation 638. If the moving average of acceleration vectors is less than the excitement threshold, then the average acceleration was not exciting enough, and operation 640 has the list of acceleration points wiped out, returning the process to operation 608.

If this moving average does exceed the excitement threshold, then the series of acceleration vectors has been deemed "exciting" enough. Operation 642 then determines whether a tagged moment has occurred too recently. This operation utilizes a debounce function. If the difference in the current time and the time an exciting moment last occurred does not exceed the debounce time, then the moment is too close, and for now is not added. Operation 644 does not wipe out the list of acceleration points, and merely returns the process to operation 608. If the difference in the current time and the time an exciting moment last occurred does exceed the debounce time, then the moment sufficiently far from the last tagged moment, and the process proceeds to saving the tagged moment.

Operation 646 involves calculating how much the excitement threshold was exceeded by, which is simply subtracting the excitement threshold from the moving average.

With the various values calculated, and a determination made, the values are ready for storing in in the memory. Operation 648 stores a tag point, which includes the moving average, the excitement threshold, how much the excitement threshold was exceeded by the moving average, a timestamp indicated when the tag point occurred, and the latitude and longitude of the vehicle when the tag point was generated in a database. This tag point database is used by the post-processing algorithm 650. Next, operation 652 sets the time an exciting moment last occurred to the current time. At this point, operation 654 returns the process to operation 608, unless the drive has been completed. In that case, the process proceeds to post-processing, described in FIG. 7.

Although not shown in FIG. 6, the mobile device 300 also receives biometric data from the smartwatch 301, and the mobile device 300 is configured to calculate tag points based upon the biometric data according to the process set forth in FIG. 4C and described above.

Figure 7:
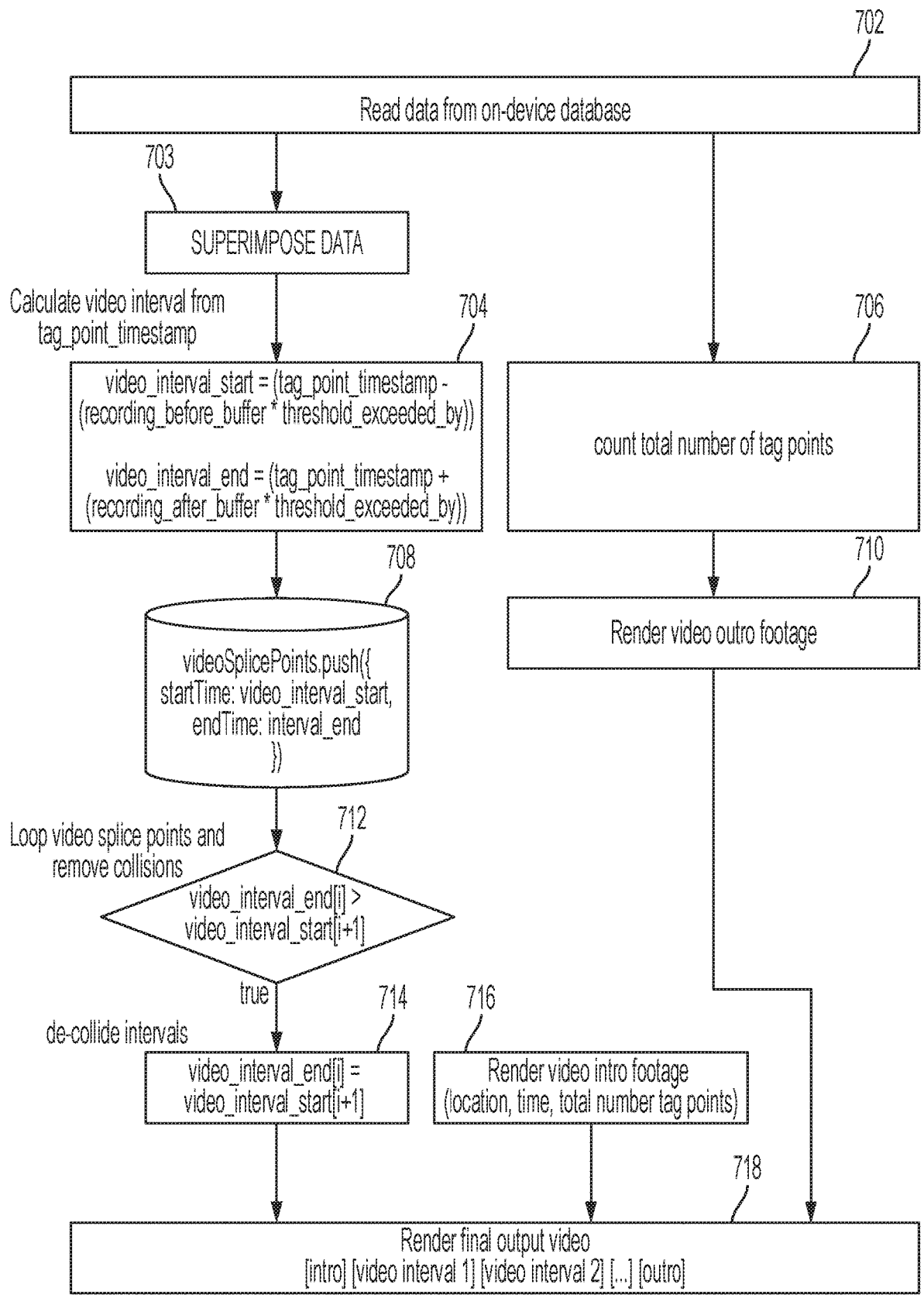
FIG. 7 is a flowchart of the post-processing portion of the video curation process, as performed using the mobile device and biometric tags.

FIG. 7 is a flowchart depicting how, in an embodiment where the sensors of the mobile device 300 and smartwatch 301 were used, specific moments from a video that were tagged to be used in curation are post-processed. Operation 702 reads the data from the database of tag points, which is populated in operation 648 of FIG. 6 and operation 492 of FIG. 4C. This operation also reads in the entire raw video file, to be curated using those tag points. At operation 703, the real-time motion-related data (e.g., vehicle speed, acceleration, and steering wheel angle) collected at steps 608 and/or real-time biometric data (e.g., heart rate) collected at step 490 are superimposed onto the video footage. Alternatively, the operation 703 may be completed immediately prior to step 718 such that the real-time motion-related data and/or real-time biometric data is only superimposed on the final clips of the video. The real-time motion-related data and/or real-time biometric data can be placed at the appropriate points within the video using the time-stamp information as a guide.

Then, in operation 704, the timestamp of a tag point is taken. This timestamp has a start and finish timestamp calculated based on the timestamp: the start timestamp is a buffer period of time (in this embodiment 2500 milliseconds) multiplied by how much the excitement threshold was exceeded by the moving average, earlier than the tag point time stamp. So, if the amount the excitement threshold was exceeded by the moving average is two, then the start timestamp is 5000 milliseconds before the tag point time stamp (2.0×2500 milliseconds). Equivalently, the end timestamp is the buffer period of time multiplied by how much the excitement threshold was exceeded by the moving average, later than the tag point time stamp. If the amount the excitement threshold was exceeded by the moving average is two, then the final span of time is 10000 milliseconds:5000 milliseconds before the tag point time stamp, and 5000 milliseconds after the tag point time stamp. This range is then pushed into a list in operation 708. Operations 704 and 708 are repeated for every tag point.

In operation 712, each time range is compared to the other time ranges. If a time range's end is after the next time range's beginning, then the time range's end is set to be equal to the next time ranges beginning in operation 714. This de-collides the ranges of time, and removes overlaps. Operations 712 and 714 generally depict de-collision of timespans. While edge cases exist (e.g. three timespans, each three seconds long, each starting one second after the other) that are not fully covered by these brief explanations of de-collision, conventional algorithms and methods may be used by a person of ordinary skill in the art to sufficiently detect overlapping spans, remove the overlaps, and create a smooth continuum of spans with no collisions. The intervals are then used to select corresponding segments of footage from the raw video file, and these segments are used in operation 718.

In operation 716, video intro footage is rendered. This footage is to be placed ahead of the footage from operation 714 by operation 718. The intro footage contains metadata about the drive such as location, time, the total number of tag points, biometric data described at operation 483, and possibly branding and copyright information.

Operation 706 descends from operation 702. Here, the tag points are counted, to be used in the outro footage.

Operation 710 renders video outro footage. This footage is to be placed behind the footage from operation 714 by operation 718. The outro footage has the tag point count from operation 706 visually rendered into the video outro footage. The outro might contain branding and copyright information.

Operation 718 is the final operation, which takes the intro footage from operation 716, appends the drive footage from operation 714 sequentially, and then appends the outro footage from operation 710. This operation creates a final contiguous video file, which is then stored in a database, and optionally displayed on a video display.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that has, comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like, whether or not qualified by a term of degree (e.g. approximate, substantially or about), may vary by as much as ±10% from the recited amount.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A method for curating a video of a vehicle drive, the method comprising:
    capturing video data of the vehicle drive over a first period of time;
    capturing biometric data associated with a driver or passenger of the vehicle over the first period of time;
    capturing motion data for the vehicle over the first period of time;
    selecting a first subset of the video data captured during the first period of time, based on (i) a corresponding first subset of the biometric data captured during the first period of time and (ii) a corresponding first subset of the motion data captured during the first period of time, the first subsets each spanning a second period of time that is less than the first period of time, wherein the first subset of the video data captured during the first period of time is selected when (i) the first subset of the motion data exceeds a threshold value for vehicle acceleration and/or vehicle steering angle, and (ii) the first subset of the biometric data exceeds a threshold value for heart rate or an acceleration of heart rate;
    storing the first subset of the video data; and
    creating a video composition including the first subset of the video data.

2. The method of claim 1, wherein the first subset of the video data captured during the first period of time is selected when the corresponding first subset of the biometric data deviates from the biometric data captured before or after the first subset of the biometric data by more than a predetermined value.

3. The method of claim 1, wherein the first subset of the video data captured during the first period of time is selected when the corresponding first subset of the motion data deviates from the motion data captured before or after the first subset of the motion data by more than a predetermined value.

4. The method of claim 1, further comprising superimposing the biometric data onto the video.

5. The method from claim 1, further comprising:
    selecting a second subset of the video data captured during the first period of time based on a corresponding second subset of the biometric data captured during the first period of time, the second subset spanning a third period of time; storing the second subset of the video data in the memory; and incorporating the second subset of the video data into the video composition.

6. The method from claim 5, further comprising:
    identifying a subset overlap where video data from a fourth period of time is present in the first subset of the video data and the second subset of the video data; and
    combining the first subset of the video data and the second subset of the video data into the video composition which only includes one instance of the video data from the fourth period of time.

7. The method of claim 1, wherein the first subset of the video data is selected when (i) a moving average of a quantity, which is calculated as a function of both a longitudinal acceleration and a lateral acceleration of the vehicle occurring during the second period of time, exceeds the threshold value for vehicle acceleration, and (ii) the first subset of the biometric data exceeds the threshold value for heart rate or the acceleration of heart rate.

8. The method of claim 7, further comprising selecting a second subset of the video data captured during the first period of time based on a corresponding second subset of the motion data and a corresponding second subset of the biometric data that are each captured during the first period of time, the second subset spanning a third period of time, wherein the second subset of the video data is selected when (i) a moving average of a quantity, which is calculated as a function of both the longitudinal acceleration and the lateral acceleration of the vehicle occurring during the third period of time, exceeds the threshold value for vehicle acceleration, and (ii) the second subset of the biometric data occurring during the third period of time exceeds the threshold value for heart rate or the acceleration of heart rate; and
    incorporating the second subset of the video data into the video composition.

9. The method of claim 7, wherein: the first subset of the video data is also selected when both (i) the quantity that is a function of both the longitudinal acceleration and the lateral acceleration of the vehicle occurring during the second period of time, exceeds a second threshold value that is lower than said threshold value, and (ii) the steering angle during the second period of time exceeds a steering angle threshold value.

10. The method of claim 7, wherein the quantity is calculated using a Pythagorean equation using the longitudinal acceleration and the lateral acceleration of the vehicle as inputs to the equation.

11. A video curation system for a vehicle, comprising:
    an input device configured to receive motion data of the vehicle during a vehicle drive, video data relating to the vehicle drive, and biometric data relating to either a driver or a passenger in the vehicle during the drive;
    a processor coupled to the input device;
    a memory coupled to the processor;
    a display coupled to the processor;
    a user interface coupled to the processor; and programming in the memory, wherein execution of the programming by the processor configures the video curation system to implement functions, including functions to:

capture the video data over a first period of time;

capture the motion data over the first period of time;

select a first subset of the video data captured during the first period of time based on a corresponding first subset of the motion data and a corresponding first subset of the biometric data that are each captured during the first period of time, the first subset of the video spanning a second period of time, wherein the first subset of the video data captured during the first period of time is selected when (i) the first subset of the motion data exceeds a threshold value for vehicle acceleration and/or vehicle steering angle, and (ii) the first subset of the biometric data exceeds a threshold value for heart rate or an acceleration of hear rate;

store the first subset of the video data in the memory;

present the first subset of the video data to a user via the display; and permit the user to adjust a start time and/or an end time of the first subset of the video data using the user interface.

12. The video curation device of claim 11, wherein the video curation system is integral with the vehicle.

13. The video curation device of claim 11, wherein the video curation system is configured to select multiple subsets of the video data and store the multiple subsets in the memory, and the video curation system is configured to permit the user to delete one or more of the subsets of the video data.

14. The video curation device of claim 11, wherein execution of the programming by the processor configures the video curation system to collect metadata regarding operation of the video curation device, wherein the metadata comprises an identity of music the video curation device played during the first period of time.

15. The video curation device of claim 11, wherein execution of the programming by the processor configures the video curation system to collect metadata regarding operation of the vehicle, wherein the metadata comprises one or more of an engine torque, engine speed and a drive gear.

* * * * *